US010526447B2

(12) United States Patent
Warchol et al.

(10) Patent No.: US 10,526,447 B2
(45) Date of Patent: Jan. 7, 2020

(54) MATERIALS THAT PROVIDE BIORESISTANCE AND/OR DEFOAMING AND SLOWER COOLING PROPERTIES FOR AQUEOUS QUENCHANTS

(71) Applicant: Houghton Technical Corp., Wilmington, DE (US)

(72) Inventors: Joseph F. Warchol, Oley, PA (US); Yaodong Gan, Whitehouse Station, NJ (US); Valarie Yvonne Pearson, Phoenixville, PA (US)

(73) Assignee: Houghton Technical Corp., Wilmington, DE (US)

( * ) Notice: Subject to any disclaimer, the term of this patent is extended or adjusted under 35 U.S.C. 154(b) by 680 days.

(21) Appl. No.: 15/099,555

(22) Filed: Apr. 14, 2016

(65) Prior Publication Data

US 2016/0304979 A1 Oct. 20, 2016

Related U.S. Application Data

(63) Continuation-in-part of application No. PCT/US2016/027619, filed on Apr. 14, 2016.

(60) Provisional application No. 62/147,840, filed on Apr. 15, 2015.

(51) Int. Cl.
| | |
|---|---|
| *C21D 1/60* | (2006.01) |
| *C08G 69/26* | (2006.01) |
| *C08G 73/02* | (2006.01) |
| *A01N 33/08* | (2006.01) |
| *A01N 37/44* | (2006.01) |
| *C08G 69/40* | (2006.01) |
| *A01N 25/02* | (2006.01) |
| *C08K 5/20* | (2006.01) |
| *C07C 231/02* | (2006.01) |
| *C07C 233/16* | (2006.01) |
| *C07C 233/34* | (2006.01) |
| *C08G 69/28* | (2006.01) |
| *C08L 77/06* | (2006.01) |
| *C08L 79/08* | (2006.01) |

(52) U.S. Cl.
CPC .......... *C08G 73/028* (2013.01); *A01N 25/02* (2013.01); *A01N 33/08* (2013.01); *A01N 37/44* (2013.01); *C07C 231/02* (2013.01); *C07C 233/16* (2013.01); *C07C 233/34* (2013.01); *C08G 69/265* (2013.01); *C08G 69/28* (2013.01); *C08G 69/40* (2013.01); *C08K 5/20* (2013.01); *C08L 77/06* (2013.01); *C08L 79/08* (2013.01); *C21D 1/60* (2013.01)

(58) Field of Classification Search
CPC .... C08G 73/028; C08G 69/26; C08G 69/265; C08K 5/20; C21D 1/60; A01N 25/02
See application file for complete search history.

(56) References Cited

U.S. PATENT DOCUMENTS

| | | | |
|---|---|---|---|
| 3,220,893 A | 11/1965 | Blackwood et al. | |
| 3,804,763 A | 4/1974 | Meinhardt | |
| 3,902,929 A | 9/1975 | Meszaros | |
| 3,948,800 A | 4/1976 | Meinhardt | |
| 4,087,290 A | 5/1978 | Kopietz et al. | |
| 4,107,061 A | 8/1978 | Sturwold et al. | |
| 4,239,635 A | 12/1980 | Rieder | |
| 4,374,741 A * | 2/1983 | Rieder ................ | C10M 173/02 |
| | | | 508/260 |
| 4,381,205 A | 4/1983 | Warchol | |
| 4,404,044 A | 9/1983 | Warchol | |
| 4,486,246 A | 12/1984 | Warchol | |
| 4,528,044 A | 7/1985 | Warchol | |
| 4,751,255 A | 6/1988 | Bentley et al. | |
| 4,826,545 A | 5/1989 | Foreman et al. | |
| 4,894,433 A | 1/1990 | Bornack, Jr. et al. | |
| 5,128,441 A * | 7/1992 | Speranza ............... | C08G 69/26 |
| | | | 525/420 |
| RE34,119 E | 11/1992 | Foreman et al. | |
| 5,332,430 A | 7/1994 | Gerigk et al. | |
| 5,391,826 A | 2/1995 | Speranza et al. | |
| 5,602,209 A | 2/1997 | Warchol et al. | |
| 5,633,309 A | 5/1997 | Warchol et al. | |
| 7,364,796 B2 | 4/2008 | Sasano et al. | |
| 7,595,288 B2 | 9/2009 | Fretz et al. | |
| 8,276,663 B2 | 10/2012 | Holtsclaw et al. | |
| 8,764,914 B2 | 7/2014 | Gunsalus et al. | |

(Continued)

FOREIGN PATENT DOCUMENTS

| | | |
|---|---|---|
| CN | 1671815 A | 2/2004 |
| CN | 1972721 A | 5/2005 |

(Continued)

OTHER PUBLICATIONS

Jeffamine T-5000 data sheet. Huntsman. (Year: 2011).*
International Search Report dated Jun. 24, 2016 in related International Patent Application No. PCT/US16/27619, filed Apr. 14, 2016.
Written Opinion dated Jun. 24, 2016 in related International Patent Application No. PCT/US16/27619, filed Apr. 14, 2016.

(Continued)

Primary Examiner — Kara B Boyle
(74) Attorney, Agent, or Firm — Howson and Howson LLP

(57) ABSTRACT

Methods and compositions are provided for heat treating, e.g. quenching a metal. The quenching composition includes a composition that comprises a polyamidopolyamine compound having a molecular weight of about 500 to about 100,000 and comprising a pendent amino group; and/or a non-polymeric amidoamine having a molecular weight of about 290 to about 5000 and comprising an amino group; and a hydroxyl containing diluent. These compositions impart one or more of the functions of quenching, lubricity, anti/low foaming and/or bioresistance to the quenching fluid.

17 Claims, 9 Drawing Sheets

(56) References Cited

U.S. PATENT DOCUMENTS

| | | | |
|---|---|---|---|
| 2005/0215670 A1* | 9/2005 | Shimasaki | C09D 5/08 |
| | | | 523/451 |
| 2007/0032428 A1 | 2/2007 | Mor et al. | |
| 2009/0095384 A1 | 4/2009 | Gunsalus et al. | |
| 2009/0198035 A1 | 8/2009 | Klein et al. | |
| 2011/0117156 A1* | 5/2011 | Lin | A61L 9/01 |
| | | | 424/409 |
| 2014/0051784 A1 | 2/2014 | Elmore et al. | |

FOREIGN PATENT DOCUMENTS

| | | |
|---|---|---|
| CN | 103282193 A | 11/2011 |
| CN | 103261317 A | 8/2013 |
| EP | 0301716 | 2/1989 |
| WO | WO2005/118008 | 12/2005 |
| WO | WO2012/071261 | 5/2012 |
| WO | WO2012/082342 | 6/2012 |
| WO | WO2016/168514 | 10/2016 |

OTHER PUBLICATIONS

Calabretta, MK et al, Antibacterial Activities of Poly(amidoamine) Dendrimers Terminated with Amino and Poly(ethylene glycol) Groups, *Biomacromolecules*, Jun. 2007; 8(6):1807-1811.

European Search Report, dated Jul. 23, 2018, in related European Patent Application No. 16780782.5, filed Apr. 14, 2016 (national phase of PCT/US2016/027619).

M. Eshraghi-Kakhki et al, Application of Polymeric Quenchants in Heat Treatment of Steels, International Journal of ISSI, Jan. 2009, 6(1):34-8.

International Preliminary Report on Patentability, dated Oct. 26, 2017, in related International Patent Application No. PCT/US16/27619, filed Apr. 14, 2016.

Response to the Non-Final Office Action filed Feb. 8, 2019, in related European counterpart Patent Application No. PCT/US2016027619.

Chinese Non-Final Office Action in related CN Application 201680021698.2, dated Sep. 30, 2019.

U.S. Non-Final Office Action in related U.S. Appl. No. 15/564,318, dated Oct. 16, 2019.

* cited by examiner

Formula I:
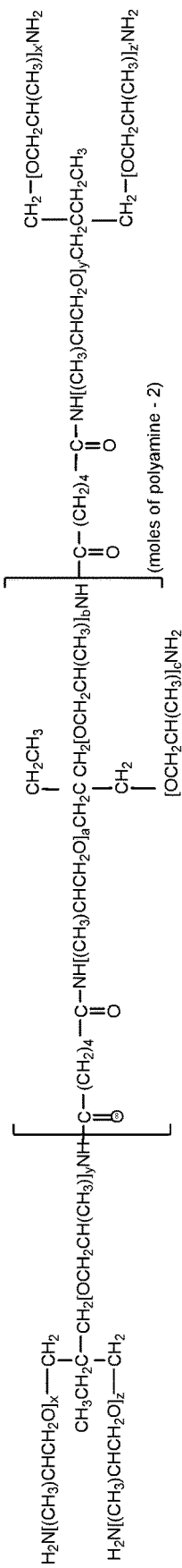
Formula II:
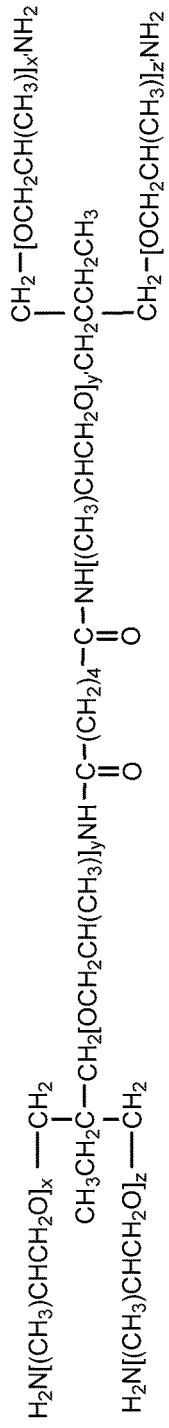
Formula III:
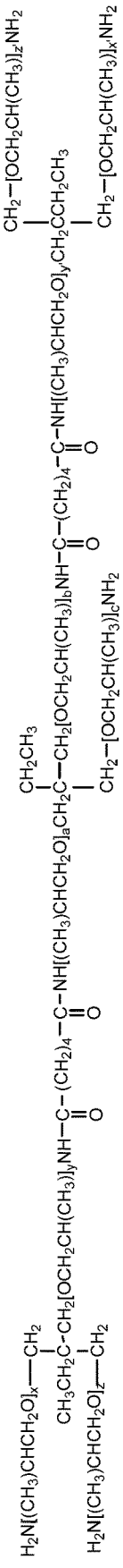
FIG. 6A
FIG. 6B
FIG. 6C Formula IV Formula V:

Formula A - Polyamidopolyamine

Formula B - Polyamidopolyamine

Formula C -- Polyamidopolyamine

Formula D - Polyamidopolyamine

Formula E - Imide-containing polyamidopolyamine

Formula F – Non-polymeric amidoamine

Formula G - Non-polymeric amidoamine

MATERIALS THAT PROVIDE BIORESISTANCE AND/OR DEFOAMING AND SLOWER COOLING PROPERTIES FOR AQUEOUS QUENCHANTS

CROSS-REFERENCE TO RELATED APPLICATIONS

This application is a continuation-in-part of International patent application No. PCT/US16/27619, filed Apr. 14, 2016, which claims the benefit of the priority of U.S. Provisional Patent Application No. 62/147,840, filed Apr. 15, 2015. These applications are incorporated herein by reference.

BACKGROUND OF THE INVENTION

This invention relates to aqueous quenching media and processes using the same for quenching metal substrates.

Various methods of heat treating metal substrates are known and include heating a metal substrate to an elevated temperature and then cooling. The cooling step, which is known in the art as "quenching", typically is performed rapidly and is accomplished by immersing a hot metal substrate in a liquid quenching medium, i.e. a quenching bath, which typically is water or oil.

When the quenching medium is water alone, very rapid cooling of the metal substrate occurs. Rapid cooling is not suitable for many types of steel, since it tends to produce excessive strain which distorts and/or cracks the metal, typically steel or aluminum. When the quenching medium is a hydrocarbon oil, a slower rate of cooling occurs. This can impart certain desirable physical properties to the metal substrate, including ductility in steel. Even though the slower cooling rate provided by oil quenching prevents or reduces excessive strain in the metal substrate, it often has the undesirable side-effect of preventing the metal substrate from adequately hardening.

Various aqueous media are available for quenching metal substrates and may include one or more of a polymer. One of the primary purposes of any quenchant is to mediate heat transfer and enhance the surface uniformity throughout the quenching process. For polymer quenchants, this is achieved by the formation and subsequent breakage and removal of an insulating film surrounding the hot metal part upon initial immersion.

Forming is a common problem encountered in quenching. Forming may be due to either chemical contamination or equipment design. Sources of chemical contamination include: detergents from cleaning solutions, metal working fluids, hydraulic fluids, i.e., process fluids. Equipment design problems include undersized reservoirs, return lines entering above the liquid level, air leaks and pump cavitation. Form formation around the metal substrate during quenching is undesirable because it enhances non-uniform cooling, resulting in increased distortion or cracking.

Another common issue in the quenching of metal substrates is microorganism proliferation. Particularly in aqueous metalworking fluids due to the water content, elevated temperatures, and contaminants, microbial contamination is common. Biocide products are often added to metalworking fluids, including aqueous quenchants, to protect against the uncontrolled growth of these organisms and prolong fluid life. They prevent corrosion and odors, extend fluid life and reduce down time caused by clogged or plugged lines or filters.

Bacterial actions alter fluid by destroying lubricants and corrosion inhibitors, and by generating corrosive organic acids, and salts. Because a cooling system cannot be stable or give consistent, predictable results with a significant bacteria load, controlling bacterial growth is critical for the long-term success of a coolant management program.

Commercial metal quenching compositions thus include a variety of components to handle the requirements of quenching, as well as to mediate the issues of forming and bacterial contamination. The addition of defoamers and antimicrobial or bioresistant components to aqueous quenching compositions adds to their expense and often to problems with environmental and health issues for workers in the quenching industries. There remains a current need for materials and methods to provide antifoam/defoaming properties and bioresistance to metalworking fluids, particularly fluids operating with agitation, such as quenchants.

SUMMARY OF THE INVENTION

It has been found by the inventors that the polyamidopolyamine compounds or non-polymeric amidoamines described herein and in U.S. Provisional Patent Application No. 62/147,840 (incorporated by reference herein in its entirety) are suitable components in aqueous quenching media to provide defoaming (antifoaming) and/or bioresistant properties. The polyamidopolyamines described herein are especially useful in quenching alloys of low hardenability.

In one aspect, a composition useful in quenching a metal or in other heat treatments of a metal comprises a polyamidopolyamine compound having a molecular weight of about 500 to about 100,000 and at least one pendant amino group, and an optional hydroxyl containing diluent.

In another aspect, a composition useful in quenching a metal or in other heat treatments of a metal comprises a non-polymeric amidoamine having a molecular weight of about 290 to about 5000 and comprising at least one amino group, and an optional hydroxyl containing diluent.

In one aspect, the polyamidopolyamine or non-polymeric amidoamines described here provide low-foaming, non-foaming, or defoaming properties to a metalworking or quenching fluid.

In another aspect, the polyamidopolyamine or non-polymeric amidoamines described here provide bioresistant or biocide properties to a metalworking or quenching fluid.

In another aspect, a composition is provided which contains the polyamidopolyamine or non-polymeric amidoamines described herein and an additional quenching agent. In another aspect, a composition is provided which contains the polyamidopolyamine or non-polymeric amidoamines described herein and other traditional quenching composition components.

In yet a further aspect, concentrates for preparing aqueous quenching media useful in the heat treatment of metal substrates are provided which include the polyamidopolyamine or non-polymeric amidoamines described herein.

In another aspect a method for quenching a metal is provided. The method includes quenching said metal with a composition which includes a polyamidopolyamine compound having a molecular weight of about 500 to about 100,000 and comprising at least one amino group.

In another aspect, a method for quenching a metal is provided. The method includes quenching said metal with a composition which includes a non-polymeric amidoamine having a molecular weight of about 290 to about 5000 and comprising an amino group.

Other aspects and advantages of the invention will be readily apparent from the following detailed description of the invention.

BRIEF DESCRIPTION OF THE DRAWINGS

FIGS. 6A, 6B and 6C, respectively, shows polyamidopolyamine compounds of Formulae I, II and III as discussed herein.

DETAILED DESCRIPTION OF THE INVENTION

Figure 1:
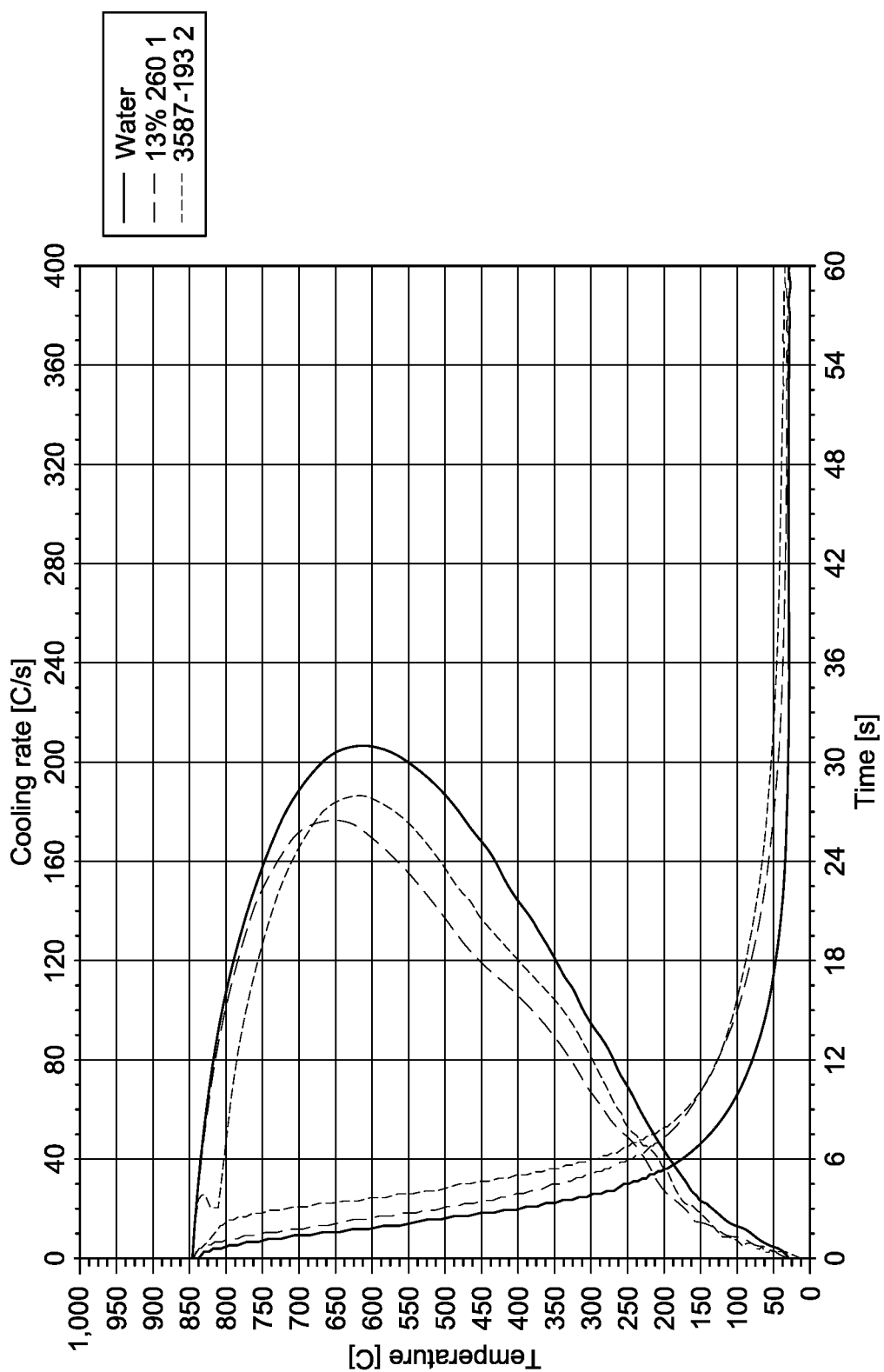
FIG. 1 is a cooling curve showing the comparison of polyamidopolyamine reaction products with water and Aqua Quench 260 (AQ260). AQ 260 is a commercial product supplied by Houghton International to slow down the quenching effect of water and its curve is shown as a broken line (i.e., large dashes). The curve for water is a solid line. The experimental polyamidopolyamine reaction product 3587-193 has a curve formed by small dashes. Product 3587-193 is a polyamidopolyamine, the reaction of Huntsman Jeffamine T403 (10 moles) with adipic acid (9 moles). The reaction is performed in approximately 44% dipropylene glycol (DPG). The DPG remains in the reaction mixture. Cloud point (1%) approximately 81° F. The cooling curve measurements were made using the IVF quenchometer.

The invention provides metalworking fluids, including aqueous quenching media, and additives therefor and processes for treating metal substrates using these aqueous quenching media. The inventors found that when used to formulate an aqueous quenching medium, the polyamidopolyamine (from polybasic acid) or non-polymeric amidoamines (from monobasic acids) described herein add desirable characteristics to the quenching medium, e.g., one or more of the characteristics of low foaming or defoaming and/or bioresistance. Thus, these compositions have an advantage of using less total components than known commercial quenchents. Therefore, the aqueous quenching media, and additives therefor, described herein find use in industries, such as automotive, aerospace, bearing industries, gear industries, and industries involving the controlled heating and cooling of metal for the purpose of obtaining specific properties.

All scientific and technical terms used herein have their known and normal meaning to a person of skill in the fields of chemistry, industrial chemistry and metal working and by reference to published texts, which provide one skilled in the art with a general guide to many of the terms used in the present application The term "metal substrate" or "metal" as used herein refers to any metal, metal alloy or metal substrate that can be heated to a high temperature, e.g., up to 1600° C., requiring cooling (e.g., quenching) in a fluid. In one embodiment, the metal substrate contains only one metal. In another embodiment, the metal substrate contains more than one metal, i.e., a metal alloy. For example, the metal substrate may contain one or more of iron, manganese, copper, silicon, sulfur, phosphorus, aluminum, chromium, cobalt, columbium, molybdenum, nickel, titanium, tungsten, vanadium, zirconium, lead, tin, or zinc, among others. Specific examples of metals that can be treated with the compositions described herein include those described in "The Heat Treater's Guide", American Society for Metals, 1982, which is hereby incorporated by reference. Employing the methods and system described herein, the resultant metal is not negatively impacted, i.e., it retains its desired porosity ductility, strength such as an excellent strength-to-weight ratio, weight, shape, corrosion resistance mechanical properties, such as good thermal electrical conductivity, high temperature resistance, hardness, wear resistance, durability, and dimensional stability, among others.

The term "alkyl" is used herein to refer to both straight- and branched-chain saturated aliphatic hydrocarbon groups. In one embodiment, an alkyl group has 1 to about 30 carbon atoms (i.e., $C_1$, $C_2$, $C_3$, $C_4$, $C_5$ $C_6$, $C_7$, $C_8$, $C_9$, or $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$). In a further embodiment, an alkyl group has 1 to about 10 carbon atoms (i.e., $C_1$, $C_2$, $C_3$, $C_4$, $C_5$ $C_6$, $C_7$, $C_8$, $C_9$, or $C_{10}$). In another embodiment, an alkyl group has 4 to about 10 carbon atoms (i.e., $C_4$, $C_5$, $C_6$, $C_7$, $C_8$, $C_9$, or $C_{10}$). In a further embodiment, an alkyl group has 5 to about 10 carbon atoms (i.e., $C_5$, $C_6$, $C_7$, $C_8$, $C_9$, or $C_{10}$).

The term "cycloalkyl" is used herein to refer to cyclic, saturated aliphatic hydrocarbon groups. In one embodiment, a cycloalkyl group has 5 to about 10 carbon atoms (i.e., $C_5$, $C_6$, $C_7$, $C_8$, $C_9$, or $C_{10}$).

The term "alkenyl" is used herein to refer to both straight- and branched-chain alkyl groups having one or more carbon-carbon double bonds. In one embodiment, an alkenyl group has 2 to about 30 carbon atoms (i.e., $C_2$, $C_3$, $C_4$, $C_5$ $C_6$, $C_7$, $C_8$, $C_9$, or $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$). In a further embodiment, an alkenyl group has 2 to about 10 carbon atoms (i.e., $C_2$, $C_3$, $C_4$, $C_5$ $C_6$, $C_7$, $C_8$, $C_9$, or $C_{10}$). In another embodiment, an alkenyl group has 4 to about 10 carbon atoms (i.e., $C_4$, $C_5$, $C_6$, $C_7$, $C_8$, $C_9$, or $C_{10}$). In a further embodiment, an alkenyl group has 5 to about 10 carbon atoms (i.e., $C_5$, $C_6$, $C_7$, $C_8$, $C_9$, or $C_{10}$). In another embodiment, an alkenyl group has 1 or 2 carbon-carbon double bonds.

The term "alkynyl" is used herein to refer to both straight- and branched-chain alkyl groups having one or more carbon-carbon triple bonds. In one embodiment, an alkynyl group has 2 to about 30 carbon atoms (i.e., $C_2$, $C_3$, $C_4$, $C_5$ $C_6$, $C_7$, $C_8$, $C_9$, or $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$). In a further embodiment, an alkynyl group has 2 to about 10 carbon atoms (i.e., $C_2$, $C_3$, $C_4$, $C_5$ $C_6$, $C_7$, $C_8$, $C_9$, or $C_{10}$). In another embodiment, an alkynyl group has 4 to about 10 carbon atoms (i.e., $C_4$, $C_5$, $C_6$, $C_7$, $C_8$, $C_9$, or $C_{10}$). In a further embodiment, an alkynyl group has 5 to about 10 carbon atoms (i.e., $C_5$, $C_6$, $C_7$, $C_8$, $C_9$, or $C_{10}$). In another embodiment, an alkynyl group contains 1 or 2 carbon-carbon triple bonds.

The term "aryl" as used herein refers to an aromatic, carbocyclic system, e.g., of about 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring has 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "thioaryl" as used herein refers to the S(aryl) group, where the point of attachment is through the sulfur-atom and the aryl group can be substituted as noted herein. The term "alkoxy" as used herein refers to the O(alkyl)

group, where the point of attachment is through the oxygen-atom and the alkyl group can be substituted as noted herein. The term "thioalkyl" as used herein refers to the S(alkyl) group, where the point of attachment is through the sulfur-atom and the alkyl group can be substituted as noted herein.

The term "hydroxyalkyl" refers to -(alkyl)OH, where the point of attachment is group through the alkyl group and the alkyl groups is defined above.

The term "alkylcarbonyl" or "arylcarbonyl" as used herein refers to the group

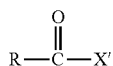

in which R is an alkyl or aryl and X' refers to the leaving group(s), as described below. "Leaving group" refers to the group displaced by the amine in the reactions described herein. This includes esters, acid halides, lactones, anhydride, cyclic anhydrides, or linear polyanhydrides, etc. Some examples are:

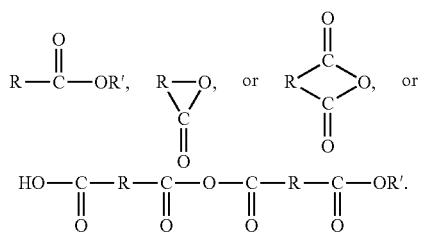

The term "optionally substituted" as used herein refers to the base group having one or more substituents including, without limitation, H, halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, aryl, heterocyclic, heteroaryl, alkoxy, aryloxy, alkylcarbonyl, alkylcarboxy, arylthio, alkylamino, or $—SO_2$-(optionally substituted $C_1$ to $C_{10}$ alkyl).

As referred to herein, the molecular weight of the polyamidopolyamines and non-polymeric amidoamines are measured using either the Organization for Economic Cooperation and Development gel permeation column (GPC) method (OECD Test 118) or by NMR and mass spectrometry, i.e., MALDI-TOF. It is anticipated that the GPC measurements (OECD 118) are likely to be most accurate. "Weight average molecular weight" as used herein means the average of the molecular weights of all of the polyamidopolyamines and/or non-polymeric amidomines present in a single condensation reaction. The molecular weight ranges cited herein and weight average molecular weights are expected to be understood to be broad enough to cover measurements made by either GPC or mass spectrometry methods or by other acceptable measurement technologies.

The term "molar basis" or "molar ratio" as used herein refers to the molar concentration of polybasic acid to primary amine. For example, where the reaction is between a dibasic acid (1 mole) and a polyamine (2 moles) having at least three primary amine groups, the molar ratio is 1:2. Where a tribasic acid is employed in the condensation reaction with a polyamine having at least three primary amine groups, the molar ratio is 1:3. Where a tetrabasic acid is employed in the condensation reaction with a polyamine having at least three primary amine groups, the molar ratio is 1:4, and so on. This ratio can be reduced to 1:1 when the reaction occurs in the presence of an organic hydroxyl solvent. In some embodiments, excess polyamine allows the reaction mixtures to be fluid. The use of organic hydroxyl solvents accomplishes the same purpose, i.e., reduces viscosity.

If the reaction employs only monobasic acids ("capping") with primary amine or polyamine, the term "molar basis" is alternatively defined as follows: The moles of monobasic acid are equal to the number of primary amino groups on the polyamine minus at least one (1). For example, when the number of primary amino groups on the polyamine is 2, the moles of monobasic acid is 1. When the number of primary amino groups on the polyamine is 3, the moles of monobasic acid are either 2 or 1. When the number of primary amino groups on the polyamine is 4, the moles of monobasic acid are 3, 2 or 1. When the number of primary amino groups on the polyamine is 5, the moles of monobasic acid are 4, 3, 2 or 1, etc. The molar basis employed in the reaction provides the resulting non-polymeric amidoamine with at least one free primary amino group. The presence of the at least one free primary amino group in the non-polymeric amidoamine provides some degree of antimicrobial activity, which increases with the number of free primary amino groups. Where there are no primary amino groups left in the reactant of this reaction between monobasic acid and primary amine or polyamine, the reactant or composition containing the reactant does not have anti-microbial properties, but the other properties, e.g., defoaming and/or lubricating properties remain.

The term "polybasic acid", as used in these preparative methods, is an acid composed of two or more C(O)OH groups or derivatives thereof. A C(O)OH derivative includes, without limitation, an ester, anhydride, acid halide, lactone, polyanhydride, or lactam thereof. Among suitable polybasic acids for the methods described herein are malonic acid, succinic acid, glutaric acid, adipic acid, pimelic acid, suberic acid, azelaic acid, sebacic acid, undecanedioic acid, dodecanedioic acid, brassylic acid, thapsic acid, phthalic acid, isophthalic acid, terephthalic acid, hemimellitic acid, trimellitic acid, trimesic acid, tartartic acid, malic acid, gluconic acid, citric acid, cysteine, aspartic acid, glutamic acid, mucic acid, or combinations thereof. Additionally, combinations of two or more of these polybasic acids are also useful in the preparative methods for the polyamidopolyamines.

In one embodiment, the molecular weight (MW) of the selected polybasic acid is from about 90 to about 314 MW. In another embodiment, the molecular weight of the selected polybasic acid is from about 104 to about 272 MW. In still other embodiments, the MW is 90, 104, 118, 132, 146, 160, 174, 188, 202, 216, 230, 244, 258, 272, 286, 300, 314 or more, including any whole numbers between and including any two endpoints in the range selected from this list (or fractional numbers representing isotopes or averages).

By "additively" as used herein to define substituents of a formula, is meant that the values of the referenced subscripts, e.g., x+y+z equal a number between, and including, two specified endpoints in the range. Each subscript may be the same or a different number as other subscripts forming the sum, provided that the sum of all subscripts is between the lowest and highest point in the range, including the endpoints in the range.

By "independently" as used herein to define substituents of a formula, means that each substituent may be any one of a following list of identified substituents, independent of other substituents in a group. For example, "R1 and R2 are independently, alkyl, aryl or alkenyl", means that R1 and R2 may be the same or different but must be one of alkyl, aryl or alkenyl.

The term "monobasic acid", as used herein, is an acid composed of one C(O)OH group or derivative thereof. Monobasic acids are useful in the condensation reactions with a primary amine to produce the non-polymeric amidoamines. Alternatively, monobasic acids are useful for terminating the dendrimer reaction to create polyamidopolyamines. In another alternative, the monobasic acids are useful in condensation reactions with other polybasic acids to produce compositions comprising polyamidopolyamines and non-polymeric amidoamines. Suitable monobasic acids for these purposes include, without limitation, acetic acid, propionic acid, butyric acid, isobutyric acid, n-valeric acid, trimethylacetic acid, caproic acid, heptanoic acid, caprylic acid, pelargonic acid, capric acid, lauric acid, myristic acid, palmetic acid, stearic acid, decylenic acid, stillingic acid, palmitoleic acid, oleic acid, ricinoleic acid, petroselinic acid, vaccenic acid, linoleic acid, linolenic acid, eleostearic acid, punicic acid, licanic acid, parinaric acid, glycolic acid, lactic acid, methoxyacetic acid, thioglycoloic acid, phenylacetic acid, glucine, alanine, valine, leucine, isoleucine, phenylalanine, tyrosine, proline, hydroxyproline, threonine, cysteine, tryptophane, arginine, lysine, histidine, gluconic acid, glyceric acid, or combinations thereof. Additionally, combinations of two or more of these monobasic acids are also useful in the preparative methods described herein.

In one embodiment, the molecular weight (MW) of the selected monobasic acid is from about 46 to about 312 MW. In another embodiment, the molecular weight of the selected monobasic acid is from about 74 to about 270 MW. In still other embodiments, the MW is 46, 60, 74, 88, 102, 116, 130, 144, 158, 172, 186, 200, 214, 228, 242, 256, 270, 284, 298, 312 or more, including any whole numbers between and including any two endpoints in the range selected from this list (or fractional numbers representing isotopes or averages).

The term "amino group" as used herein means the formula —NRR', where in R and R' are independently H, or a $C_1$ or $C_2$ alkyl. In some embodiments, the amino groups are primary, wherein the nitrogen has two reactive hydrogens, e.g., —$NH_2$. In other embodiments, the amino groups are secondary, e.g., —$NHCH_3$, wherein the nitrogen has a single reactive hydrogen. In still other embodiments, the amino groups are tertiary, e.g., —$N(CH_3)CH_3$. Wherever in the formulae and other examples of polyamidopolyamines, the amino group is shown as $NH_2$, it should be understood to include replacement thereof with secondary or tertiary amino groups by way of alkylating with alkyl halides (alkylation of amines) up to and including quaternary ammonium salts. The term "pendant amino group" is meant to refer to amino groups attached to a polymeric unit, and can repeat at regular intervals or intermittently along the polymer chain, also including terminal amino groups. The term "unreacted amino group" means a primary amino group, $NH_2$. The amino group can also be converted to a salt with acid(s).

The term "polyamine" as used herein refers to any compound comprising a primary amine (or amino) group. In one embodiment, the polyamine has one or more amino groups. In another embodiment, the polyamine has two or more amino groups. In still other embodiments, the polyamine has at least three primary amino groups. In another embodiment the polyamine has 5 or more primary amino groups.

The term "polyamidopolyamine" as used herein refers to a polymeric compound having at least one primary amino group(s). In one embodiment, the compound has at least two primary amino groups. In another embodiment, the compound has at least three primary amino groups. In still another embodiment, the compound has at least four primary amino groups. When the polyamidopolyamine is one of Formula A through E as described in U.S. provisional patent application No. 62/147,940, or incorporated herein by reference, and in FIGS. 8A, 8B, 8C, 9A and 9B herein, the number of primary amino groups in the polymer is between 4 and 14. When the polyamidopolyamine is prepared by the sequential (dendrimer) method described herein, the polymer may have more than 14 primary amines, based on the selection of polybasic acid and primary amine employed to generate the polymer. In certain embodiments, these polyamidopolyamine compounds are prepared by the condensation of polyamino compounds with polybasic acids.

The term "non-polymeric amidoamine" as used herein refers to a linear or branched non-polymeric compound having at least one primary amino group(s). In one embodiment, the compound has at least two primary amino groups. In another embodiment, the compound has at least three primary amino groups. In still another embodiment, the compound has at least four primary amino groups. When the non-polymeric amidoamine is one of Formula F (FIG. 9C), the number of primary amino groups in the amidoamine is 2. When the non-polymeric amidoamine is one of Formula G (FIG. 9D), the number of primary amino groups in the amidoamine is 1. Formula F and G are further described in U.S. provisional patent application No. 62/147,940, or PCT/US16/27619 incorporated herein by reference. In certain embodiments, these non-polymeric amidoamine compounds are prepared by the condensation of polyamino compounds with monobasic acids.

The term "imide" as used herein refers to a compound containing two carbonyl groups bonded to a primary amine, e.g., having the formula below, wherein R, R' and R" are independently an alkyl, heteroalkyl, alkenyl, alkynyl, cycloalkyl, heterocyclic group, aryl, heteroaryl, etc:

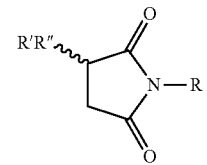

The term "diluent" or "solvent" as used herein is a hydroxyl containing diluent or solvent. In one embodiment, that diluent is water. In one embodiment, when the hydroxyl containing diluent used in the condensation reactions is water, it is added at the end of the condensation reaction. In other embodiments, water may also be present or added to the use (e.g., quenching) compositions or concentrates. In another embodiment, the hydroxyl containing diluent is an organic diluent. In embodiments where the organic diluent or solvent participates in the condensation reactions, as described below, it is not removed from the reaction mixture. Among suitable organic diluents are alcohols, polyols, carbitols, CELLOSOLVE™ Solvents (Dow Chemical), or combinations of these four types of diluents. In one embodiment, the organic diluent contains a polyol, such as a glycol. One such exemplary diluent contains a polyalkylene glycol. In another embodiment, the hydroxyl containing diluent contains ethylene glycol or diethylene glycol. In another embodiment the diluent comprises triethanolamine. In still another embodiment, the diluent contains N,N,N',N'-tetrakis (2-hydroxypropyl) ethylenediamine (also known at tetra(2-hydroxypropyl) ethylenediamine). Another diluent component is glycerin. Still other diluents may be prepared by combinations of any two or more of the above noted hydroxyl-containing diluents. One of skill in the art may readily select such diluents from among the many diluents or solvents available.

The term "water-soluble" as used herein refers to the ability of a chemical component to combine with, disperse, or be emulsified, in water. Desirably, the polyamidopolyamines and/or non-polymeric amidoamines and compositions containing them as described herein substantially dissolve in water. More desirably, the term "water-soluble" refers to a compound or composition that has 100% dissolution in water.

By "water-soluble acid" is meant an acid which when added to the quenchant compositions described and used herein enhances the water solubility of the other components, particularly the polyamidopolyamine, the amidopolyamines (from monobasic acid), and/or the non-polymeric amidoamines of the quenching compositions. In one embodiment, the water soluble acid is phosphoric acid. In another embodiment, the water soluble acid is acetic acid or glycolic acid or lactic acid. In still other embodiments, combinations of these water soluble acids are used. Other acids which enhance water solubility of the compositions described herein are intended to be incorporated by this term.

The term "antimicrobial" as used herein means an agent, component or composition that is destructive to, or inhibits the growth of, microorganisms (bacteria, virus, fungus, etc.) which come into contact with the antimicrobial agent, component or composition.

The term "bioresistance" as used herein means that the composition, agent or component does not support the growth of microorganisms on or in a substrate (e.g., a surface or fluid) treated with or containing the composition, agent or component.

The phrase "in contact with", when utilized to refer to a surface's interaction with the compositions described herein, includes any point of contact of the surface with the composition. Such contact includes, without limitation, application of the composition to the surface (e.g., metal or alloy) using conventional techniques. Such conventional techniques include, without limitation, coating, spraying, contact rolling, squeegeeing, dipping, brushing, flooding, or immersion application techniques. In one embodiment, the surface is contacted with the composition prior to further manipulation of the surface. In another embodiment, the surface, e.g., metal, is contacted with the composition during use of the surface, e.g., metal in the desired method, e.g., rolling, stamping, etc.

The term "number" as used throughout this specification and particularly in reference to molecular weights means a whole number or any fraction between two other whole numbers, when applicable. In certain embodiments, a fractional number referring to molecular weight means molecular weights of isotopes or molecular weight averages.

The terms "a" or "an" refers to one or more, for example, "an amino group" is understood to represent one or more amino groups. As such, the terms "a" (or "an"), "one or more," and "at least one" are used interchangeably herein. As used herein, the term "about" means a variability of 10% from the reference given, unless otherwise specified.

Various embodiments in the specification are presented using "comprising" language, which is inclusive of features in addition to the specifically recited features or steps. Under other circumstances, a related embodiment is also intended to be interpreted and described using "consisting of" or "consisting essentially of" language. The words "consist", "consisting", and its variants, are to be interpreted to exclude features in addition to those features specifically recited, or to include only additional features of minor significance.

The Quenching/Heat Treating Compositions

In one embodiment, the compositions described herein contain a polyamidopolyamine, which is a linear, cyclic, branched or crosslinked amide comprising a primary amino group. In certain embodiments the polyamidopolyamine comprises one or more, two or more, three or more or 14 or more amino groups, as described throughout this specification or in U.S. 62/147,840, incorporated by reference herein. In one embodiment, the compositions of polyamidopolyamine or mixtures thereof are produced by the reaction of a polybasic acid and polyamine in the presence of an optional organic diluent as described throughout this specification. In certain other embodiments, the method of making the polyamidopolyamine and mixtures thereof involves repeated cycles of condensation reactions as described in U.S. 62/147,840. In still other embodiments, the method of making the polyamidopolyamine or a composition comprising it involves a condensation reaction employing at least one polybasic acid and at least one polyamine.

In additional embodiments, the compositions described herein contain a non-polymeric amidoamine, which is a linear or branched amide comprising a primary amino group. In certain embodiments the non-polymeric amidoamine comprises one or more, two or more, three or more amino groups, as described throughout this specification. In one embodiment, the compositions of non-polymeric amidoamine or non-polymeric amide or mixtures thereof are produced by the reaction of a monobasic acid and primary amine in the presence of an optional organic diluent as described below. In still other embodiments, the method of making a composition comprising a non-polymeric amidoamine and a polyamidopolyamine involves a condensation reaction employing at least one polybasic acid, at least one monobasic acid and at least one polyamine or primary amine.

The heat treating or quenching composition, in still another embodiment, contains a mixture of multiple polyamidopolyamines and/or non-polymeric amidoamines of different formulae. In certain embodiments, the composition may also contain polyamidoamines and/or polyamidopolyamides or non-polymeric amides in admixture with these polyamidopolyamines and/or non-polymeric amidoamines. In yet a further embodiment, the composition may contain a polyamidopolyamine that further comprises an imide group. Still other embodiments of the composition contain a mixture of any number of the polyamidopolyamines, with or without imide groups, and with unreacted polyamine. Still other embodiments of the composition contain a mixture of any number of the non-polymeric amidoamines, and/or non-polymeric amides, and with unreacted polyamine. In still other embodiments, the composition may contain multiple different non-polymeric amidoamines, multiple different non-polymeric amides, multiple different unreacted primary amines, multiple different monobasic acids, or any combination thereof.

These compositions as described herein have a variety of uses. Depending upon its complete formulation, the composition containing the polyamidopolyamine and/or non-polymeric amidoamine has antimicrobial properties. In another embodiment the composition containing the polyamidopolyamine and/or non-polymeric amidoamine has bioresistant properties. In another embodiment the composition containing the polyamidopolyamine and/or non-polymeric amidoamine has low-foaming, defoaming, deaeration, or anti-foaming properties. In another embodiment the composition containing the polyamidopolyamine and/or non-polymeric amidoamine has lubricating and/or load carrying properties. In still other embodiments, the same composition has bioresistant and defoaming properties. In yet other embodiments, the same composition has bioresistant and lubricant properties. In a further embodiment, the same composition has bioresistant, lubricant and defoaming or anti-foaming properties. In another embodiment, the same composition has antimicrobial properties. In still other embodiments, the same composition has antimicrobial and defoaming properties. In yet other embodiments, the same composition has antimicrobial and lubricant properties. In a further embodiment, the same composition has bioresistant, lubricant and defoaming or anti-foaming properties.

In one embodiment, the composition is provided as a concentrate. In another embodiment, the composition comprises water or any organic diluent. In another embodiment, the composition comprises an organic hydroxyl-containing diluent. These compositions can be provided as additives containing the described polyamidopolyamines for a variety of industrial fluids and uses. Alternatively, the compositions are themselves industrial fluids based upon the inclusion of other components. For example, the compositions, depending upon the other components can be metal quenching fluids, lubricants, metal working fluids, metal drawing fluids, metal stamping fluids, metal rolling fluids, hydraulic fluids, and other process fluids that are dilutable in water.

The "metal quenching fluid" may be utilized in the quenching processes as a bath or a spray has a composition that is selected considering the particular metal or metal alloy, the size of the metal or metal alloy piece, and the size and shape, and other physical characteristics of the die being utilized. Typically, the quenching fluid in the bath and/or spray is made up of a quenching polymer or product, certain additives and a hydroxyl diluent, e.g., water.

In one embodiment, the compositions described herein employ a polyamidopolyamine compound having a molecular weight of about 500 to about 100,000 and comprising an amino group as a quenching component. Such a polyamidopolyamine thus may have a molecular weight of at 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10,000, 20,000, 30,000, 40,000, 50,000, 60,000, 70,000, 80,000, 90,000 and up to 100,000 including all numbers between any two endpoints in the range.

In another embodiment, the compositions described herein employ a nonpolymeric amidoamine compound having a molecular weight of about 290 to about 5,000 and comprising an amino group as a quenching component. Such a non-polymeric amidoamine has a molecular weight (MW) of between about 290 to about 5000, including all numbers therebetween and including the endpoints in the range. In certain embodiments, the non-polymeric amidoamine of these compositions can have MW of at least 290, 390, 490, 590, 690, 790, 890, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and up to 5000. In certain embodiments, the non-polymeric amidoamine compound can have MW of greater than 5000.

Based upon its intended use, the composition can contain from 0.5 up to about 40% of the polyamidopolyamine or non-polymeric amidoamine or a combination of both. In one embodiment, the composition contains at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or at least 40%, including any whole or fractional percentages between any two of these values.

In one embodiment, the polyamidopolyamine or non-polymeric amidoamine is water soluble. In another embodiment, the polyamidopolyamine or non-polymeric amidoamine is water dispersible. In another embodiment the composition contains a water soluble acid as defined above to enhance water solubility. Another characteristic of a suitable polyamidopolyamine is that it is non-shearing in water.

Yet another characteristic of the polyamidopolyamine is that is has a cloud point measured in water of about 180° F. or less. Polyamidopolyamines and/or non-polymeric amidoamines and the compositions described herein are further defined as having a cloud point (i.e., inverse solubility) of between about 25° C. to 82° C. (or 77° F. to 180° F.) in water. Suitable cloud points for these compositions range from about 25° C. to about 82° C., i.e., from 25, 30, 35, 40, 45, 50, 55, 60, 65, 70, 73, 80 to 82° C. including any degree between any two of these values. However, some embodiments of the compounds or compositions described herein form cloud points (i.e., appear cloudy) at ambient temperature, i.e., 25° C. These embodiments can be made clear by further cooling.

Still other polyamidopolyamines and/or non-polymeric amidoamines and/or compositions comprising one or both such compounds as described herein and as described in U.S. 62/147,840, may be defined by their method of preparation. Thus in one embodiment, the polyamidopolyamine having a molecular weight of about 500 to about 100,000 and comprising at least one, or at least two, or at least three or at least 4 or more primary $NH_2$ groups or a composition containing one or a mixture of multiple polyamidopolyamines is prepared by a condensation reaction between a polybasic acid and a polyamine.

In one embodiment, the polyamidopolyamine is a condensation product of one or more polyamine comprising at least 3 $NH_2$ groups with one or more $C_2$ to $C_{18}$ polybasic acid or derivative thereof. In another embodiment, the polyamidopolyamine is a condensation product of 2 polyamines comprising at least 3 $NH_2$ groups with one or more $C_4$ to $C_{16}$ polybasic acid or derivative thereof. In another embodiment, the polyamidopolyamine is a condensation product of one or more polyamines comprising at least 3 $NH_2$ groups with two $C_4$ to $C_{16}$ polybasic acid or derivative thereof. In still another embodiment, the polyamidopolyamine is a condensation product of one polyamine comprising at least 3 $NH_2$ groups with one polyamine comprising 2 $NH_2$ groups, and one or more $C_4$ to $C_{16}$ polybasic acid or derivative thereof. In any of these embodiments, the polybasic acid may be an acid as described above.

Various combinations of selected polybasic acids and selected polyamines or primary amines comprising one or more amino groups may participate as reactants in a suitable condensation reaction to produce the polyamidopolyamines. One of skill in the art given the teachings of this specification can readily select other polybasic acids and polyamines.

In still another method, a composition comprising a polyamidopolyamine having a molecular weight of greater than about 5000 and comprising multiple primary $NH_2$ groups and/or a composition containing it is prepared by sequential condensation reactions (i.e., a dendrimer process). According to this method, a polybasic acid is reacted with a polyamine and an optional hydroxyl-containing solvent to produce a first polyamidopolyamine as a reaction product. The polyamidopolyamine reaction product of the first reaction is then itself reacted with the same or different a polybasic acid and an optional hydroxyl-containing solvent to produce another polyamidopolyamine as a subsequent polyamidopolyamine reaction product. Additional sequential condensation reactions are performed by reacting the polyamidopolyamine reaction product of each preceding condensation reaction with the same or different polybasic acid and an optional hydroxyl-containing solvent for a selected number of iterations.

The reaction sequence may be terminated by addition of a monobasic acid or polybasic acid, by a condensation reaction or a salt reaction. This termination can occur when the composition demonstrates a desired characteristic selected from anti-foaming, low-foaming, defoaming, lubricity, bioresistance, antimicrobial activity or any desired combination of these characteristics.

The polyamines and polybasic acids used in the methods described above, including the sequential (dendrimer) reaction method, may be selected from among known compounds or those specifically identified herein. In the sequential reaction, the polyamines and polybasic acids may be the same in each sequential reaction or different. The reactants for any of the above methods can include any of the polybasic acids comprising two C(O)OH groups or derivatives thereof, as identified above.

In another embodiment a quenching composition containing one such polyamidopolyamine can be present in a hydroxyl-containing diluent comprising water, in which the mole ratio of said polyamine to polybasic acid is about 2 to 1. In another embodiment, the composition containing the polyamidopolyamine is a hydroxyl-containing diluent that lacks water and the mole ratio of said polyamine to polybasic acid is from about 1:1 to about 2:1, including all fractional numbers therebetween.

Polyamines useful in the condensation process to produce useful polyamidopolyamine include, among others, polyamines of the formulae:

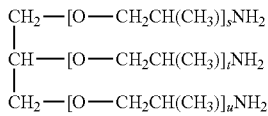

wherein the subscripts "s, t, and u" are defined additively, that is, s+t+u equal a number between 3 to about 90, including all numbers therebetween and the endpoints in the range. This additive subscript value includes both endpoints in the range and is selected from at least 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90.

Another useful polyamine has the formula:

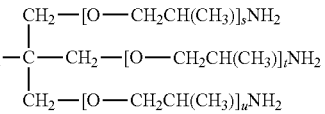

wherein r, s, t, and u are, additively, 4 to about 90 including both endpoints in the range (see the numerical range of paragraph 0092).

Another useful polyamine has the formula:

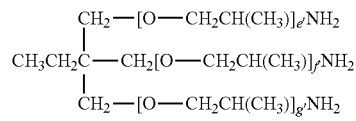

wherein, e', f', and g' are, additively 3 to about 90 including both endpoints in the range (see the numberical range) which includes both endpoints in the range and is slected from at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90).

Thus, in certain embodiments of the heat treating compositions described herein, the polyamidopolyamine comprises a pendent amino group. Polyamidopolyamines useful in these heat treating compositions include those described in U.S. 62/147,840, PCT/US16/27619 and FIGS. 6A, 6B, 6C, 7A, 7B, 8A, 8B, 8C, 9A and 9B herein, as well as those described as follows:

In one embodiment, the polyamidopolyamine is of the Formula I shown in FIG. 6A herein. The subscripts x, y, z, and x', y', z', and a, b, and c are all defined additively, that is, x+y+z equals a number from 3 to about 90 including both endpoints in the range (at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90); x'+y'+z' equals a number from about 3 to about 90 including both endpoints in the range; and a+b+c equals a number from 3 to about 90 including both endpoints in the range.

In another embodiment, the polyamidopolyamine is of the Formula II in FIG. 6B herein, wherein x, y, z, x', y', and z' are defined additively, that is, x+y+z equals a number from 3 to about 90 (at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90); and x'+y'+z' equals a number from about 3 to about 90 including both endpoints in the range ( as shown immediately above).

In another embodiment, the polyamidopolyamine is of the Formula III in FIG. 6C herein, wherein x, y, z, and x', y', z', and a, b, and c are additively 3 to about 90 including both endpoints in the range (at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90).

Figure 7A:
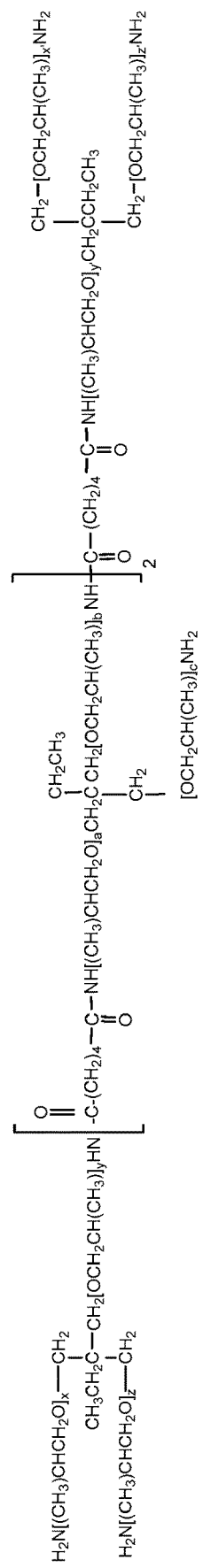
FIGS. 7A and 7B, respectively, shows polyamidopolyamine compounds of Formulae IV and V as discussed herein.

In another embodiment, the polyamidopolyamine is of the Formula IV in FIG. 7A herein, wherein x, y, z, x', y', z', a, b, and c are additively 3 to about 90, that is, x+y+z equals a number from 3 to about 90 including both endpoints in the range (see para 0092); x'+y'+z' equals a number from about 3 to about 90 including both endpoints in the range; and a+b+c equals a number from 3 to about 90 including both endpoints in the range (at least a number from 3 to about 90 (at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90); x'+y'+z' equals a number from about 3 to about 90 including both endpoints in the range; and a +b +c equals a number from 3 to about 90 including both endpoints in the range (see the range as shown immediately above).

Figure 7B:
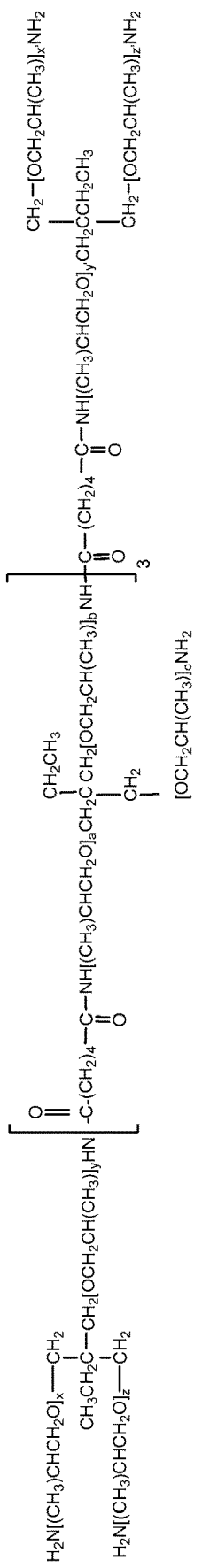
Figure 8A:
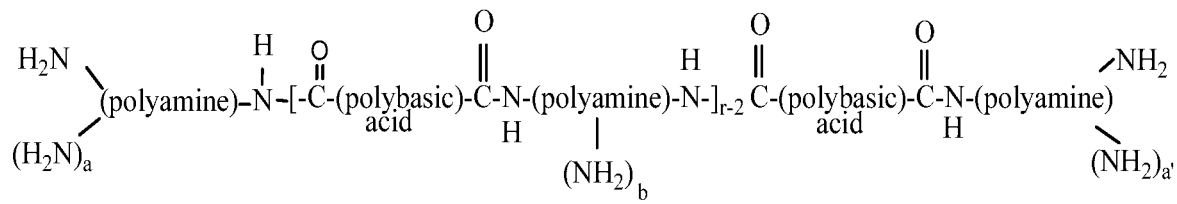
FIGS. 8A, 8B and 8C, respectively, shows the polyamidopolyamine structures for: Formula A, wherein the subscripts a and a' are independently 1 or 2; subscript b is 0, 1 or 2; and subscript r represents a number between 2 to about 10, including both endpoints of the range; Formula B, wherein subscripts a, c, d and e are each independently 1 or 2; subscript b is 0, 1 or 2; and subscript r is a number between 3 to about 10, including both endpoints of the range; and Formula C, wherein subscripts a, c, d, and e are independently a number 1 or 2; subscript b is a number 0, 1 or 2; and subscript r is a number between 4 and about 10, including both endpoints of the range.
Figure 8B:
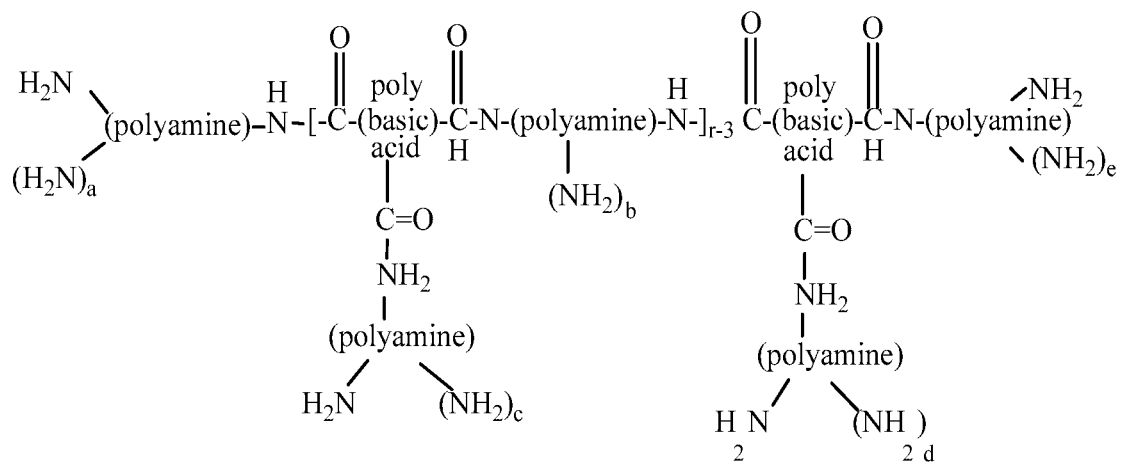
Figure 8C:
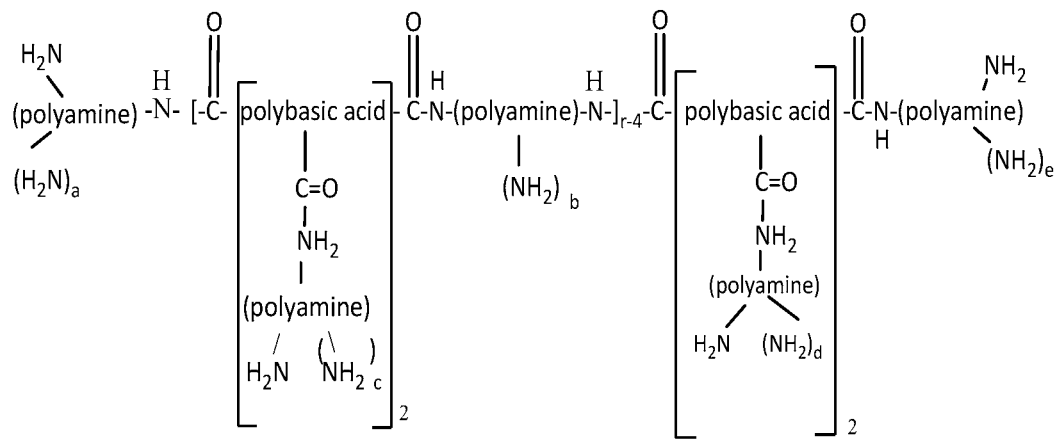

In another embodiment, the polyamidopolyamine is of the Formula V in FIG. 7B herein, wherein x, y, z, x', y', z', a, b, and c are defined the same as for Formula IV.

In another embodiment, for a 1:1 molar ratio of polyamine to dimer acid, a quenching composition can contain a polyamidopolyamine compound as described above and with a polyamidopolyamine of Formula A (FIG. 8A) and also contain a compound of Formula A':

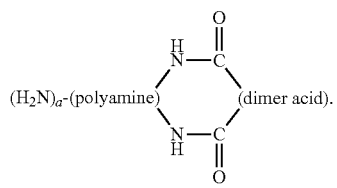

In one embodiment of this formula, the subscript a is a number from 1 to 4. For example, where the polyamine has 3 amino groups, a=3−2=1. Where the polyamine has 4 amino groups, a=4−2=2. Where the polyamine has 6 amino groups, a=6−2=4, and so on.

Figure 9A:
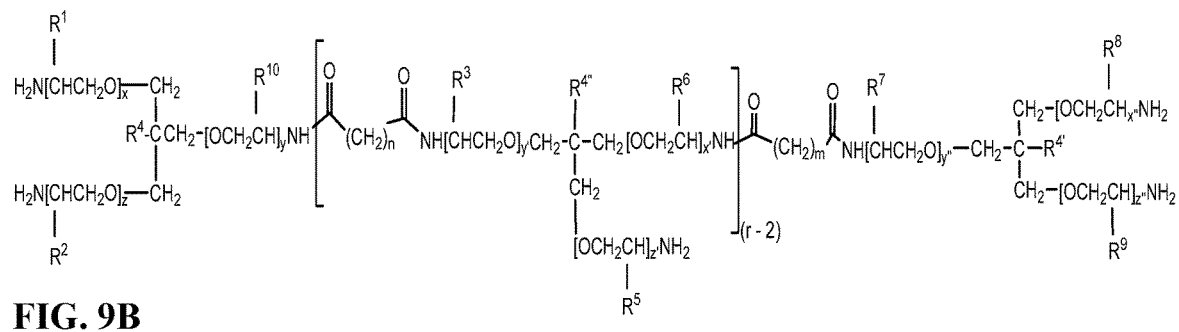
FIGS. 9A, 9B, 9C and 9D, respectively, shows the polyamidopolyamine structures: Formula D (FIG. 9A), in which $R^1$, $R^2$, $R^3$, $R^5$, $R^6$, $R^7$, $R^8$, $R^9$ and $R^{10}$ are independently, H, methyl, ethyl, propyl or butyl and $R^4$, $R^{4'}$ and $R^{4''}$ are independently methyl, ethyl, propyl or butyl; subscripts subscripts x, y, z, and x', y', z', and x", y", and z" are all defined additively, that is, x+y+z equals a number from 3 to about 90; x'+y'+z' are all defined additively, that is, x+y+z equals a number from 3 to about 90 including both endpoints of the range; x'+y'+z' equals a number from about 3 to about 90 including both endpoints of the range; and x"+y"+z" equals a number from 3 to about 90 including both endpoints of the range; n, is a number between 1 to 14, including the endpoints of the range; m represents a number selected independently of the value of n, and is also a whole number between 1 to 14 including the endpoints of the range, and r represents a number between 2 to about 10, including both endpoints of the range; and Formula E (FIG. 9B) which shows the chemical structure of an imide-containing polyamidopolyamine in which subscript t represents a whole number from 1 to about 5; and Formula F (FIG. 9C) which is the chemical structure of a non-polymeric amidoamine in which the sum of x+y+z equals a number between 3 to about 90, including both endpoints of the range; and $R^1$ is $C_1$ to $C_{11}$ alkyl or $C_1$ to $C_{11}$ substituted alkyl; and Formula G which (FIG. 9D) is another chemical structure of a non-polymeric amidoamines, in which x, y, and z, additively, equal a number between 3 to about 90, including both endpoints of the range; and $R^1$ and $R^2$ are, independently, $C_1$ to $C_{11}$ alkyl or $C_1$ to $C_{11}$ substituted alkyl.
Figure 9B:
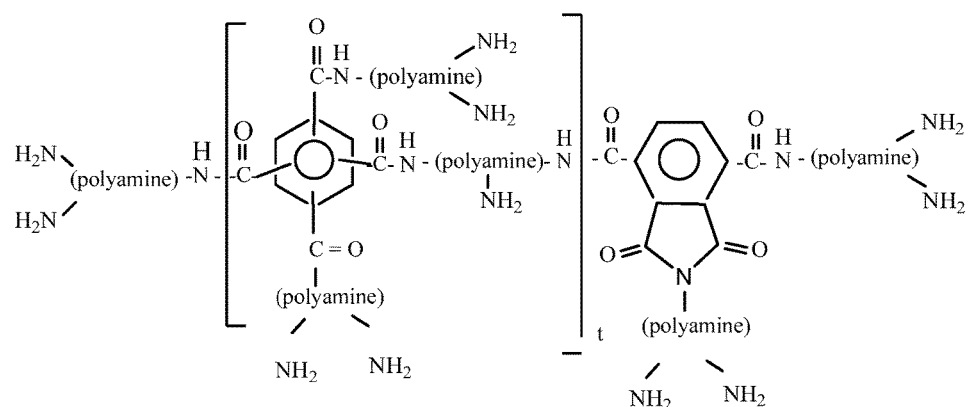
Figure 9C:
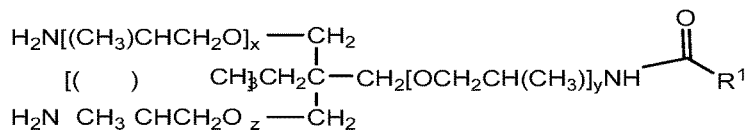
Figure 9D:
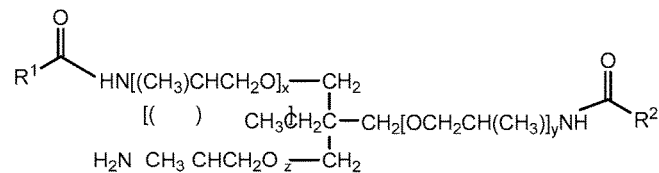

In yet another embodiment, the non-polymeric amidoamines useful in these heat treating compositions include those described in U.S. 62/147,840, as well as those described in FIGS. 9C and 9D and as follows. In still other embodiments, the non-polymeric amidoamine having a molecular weight of about 290 to about 5000 and comprising at least one, or at least two, or at least three or more primary amino groups or a composition containing one or a mixture of multiple non-polymeric amidoamines and optionally one or more of a mixture of non-polymeric amides as described herein is prepared by a similar condensation reaction between a selected monobasic acid and a primary amine, or by condensation reactions between multiple monobasic acids and one or multiple amines or polyamines, in a manner similar to the condensation reactions described above for the polyamidopolyamine-containing compositions.

In one embodiment a suitable non-polymeric amidoamine is a condensation product of one or more primary amine comprising at least 2 amino groups and one or more $C_2$ to $C_{18}$ monobasic acid or derivative thereof. In another embodiment a suitable non-polymeric amidoamine is a condensation product of two or more primary amines comprising at least 2 amino groups and one or more $C_2$ to $C_{18}$ monobasic acid or derivative thereof. In another embodiment, a suitable non-polymeric amidoamine is a condensation product of one or more primary amines comprising at least 2 amino groups and two $C_2$ to $C_{18}$ monobasic acid or derivative thereof. In still another embodiment, a suitable non-polymeric amidoamine is a condensation product of one primary amine comprising at least 2 $NH_2$ groups, and another amine comprising 2 amino groups, and one or more $C_2$ to $C_{18}$ monobasic acid or derivative thereof. In any of these embodiments, the monobasic acid or derivatives or the polybasic acid may be an acid as described above.

In another embodiment a quenching composition containing one such non-polymeric amidoamine can be present in a hydroxyl-containing diluent comprising water, in which the mole ratio of the primary polyamine to monobasic acid provides at least one free amino group, and water is added at the end of the condensation reaction. in another embodiment, the composition containing the non-polymeric amidoamine has all of its amino groups converted to amide. In this case, the condensation products retain defoaming and lubricant properties, but do not act as antagonists to microorganisms. In still another embodiment, the diluent lacks water and the mole ratio of the primary amine to monobasic acid provides at least one free amino group.

The primary amine used in the non-polymeric amidoamine condensation reactions may be a primary diamine, primary triamine, primary tetraamine or a higher primary amine. Primary amines useful in the condensation process to produce useful non-polymeric amidoamine include, among others, polyamines of the formulae below. For each of these amine formulae, the additive selections are as defined as above for subscripts in the same ranges for the polyaminopolyamides.

One such primary amine is the amine of the formulae:

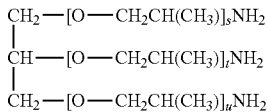

wherein the subscripts "s, t, and u" are defined additively, that is, s +t +u equal a number between 3 to about 90, including all numbers therebetween and the endpoints in the range. This additive subscript value includes both endpoints in the range and is selected from at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90. Another suitable amine is of the formula

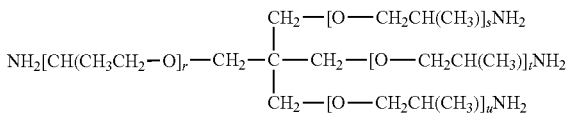

wherein r, s, t, and u are, additively, 4 to about 90 including both endpoints in the ranee which includes 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90. Still another suitable amine is of the formula

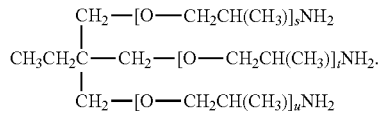

An exemplary non-polymeric amidoamine has the formula:

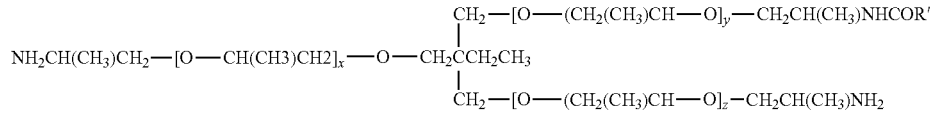

wherein x, y, and z are additively 0 to about 87, including all numbers and the endpoints in the range (see the ranges described in the preceding paragraph above), and R' is $C_1$ to $C_{11}$ alkyl or $C_1$ to $C_{11}$ substituted alkyl.

Another exemplary non-polymeric amidoamine has the formula:

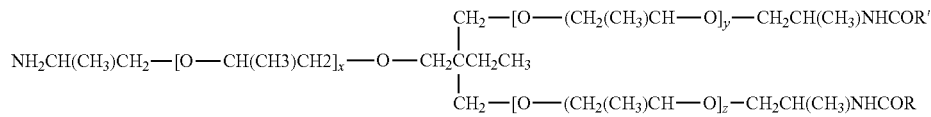

wherein x, y, and z are additively a number between 0 to about 87, including the endpoints in the range (see the ranges as defined in the preceding paragraphs above), and R and R' are independently $C_1$ to $C_{11}$ alkyl or $C_1$ to $C_{11}$ substituted alkyl.

An exemplary non-polymeric amidoamine has the formula:

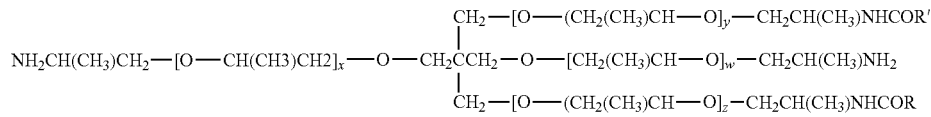

wherein w, x, y, and z are additively a number between 0 to about 86, including the endpoints in the range (see the ranges as defined in paragraphs immediately above), and R and R' are independently $C_1$ to $C_{11}$ alkyl or $C_1$ to $C_{11}$ substituted alkyl.

Still another exemplary non-polymeric amidoamine has the formula:

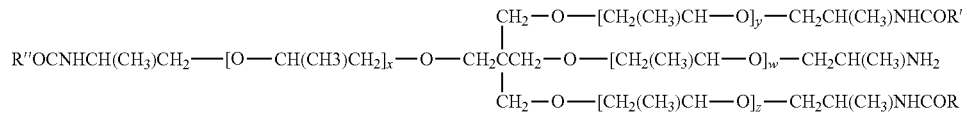

wherein w, x, y, and z are additively a number between 0 to about 86, including the endpoints in the range (see the ranges as defined in paragraphs immediately above), and R, R' and R" are independently $C_1$ to $C_{11}$ alkyl or $C_1$ to $C_{11}$ substituted alkyl.

Other characteristics of these compositions including the follows: In certain embodiments, the polyamidopolyamine and/or non-polymeric amidoamine and/or the composition containing that polyamidopolyamine and/or non-polymeric amidoamine is water-soluble. In another embodiment, the polyamidopolyamine and/or non-polymeric amidoamine and/or the compositions containing one or both of them is water dispersible. Polyamidopolyamines and/or non-polymeric amidoamines and the compositions described herein are further defined as having a cloud point (i.e., inverse solubility) of between about 25° C. to 82° C. (or 77° F. to 180° F.) in water. Suitable cloud points for these compositions range from about 25° C. to about 82° C., i.e., from 25, 30, 35, 40, 45, 50, 55, 60, 65, 70, 73, 80 to 82° C. including any whole or fractional degree between any two of these values. However, some embodiments of the compounds or compositions described herein form cloud points (i.e., appear cloudy) at ambient temperature, i.e., 25° C. These embodiments can be made clear by further cooling.

In still other embodiments the polyamidopolyamine and/or non-polymeric amidoamine and/or the compositions containing them has a pH of about 8, 8.2, 8.4, 8.6, 8.8, 9.0, 9.2, 9.4, 9.6, 9.8, 10.0, 10.2, 10.4, 10.6, 10.8, 11.0, or any number therebetween.

In some embodiments, the polyamidopolyamine or non-polymeric amidoamine are used as quenchants. In other embodiments, the quenching compositions use the polyamidopolyamine and/or non-polymeric amidoamine compound as an anti-foamer, defoamer or low foamer additive. In another embodiment, the quenching compositions use the polyamidopolyamine and/or non-polymeric amidoamine compound for both quenching properties and anti-foaming, low foaming or defoaming properties. In certain embodiments, the low-foaming, non-foaming, or defoaming properties are measured in water.

In other embodiments, the quenching compositions use the polyamidopolyamine compound and/or non-polymeric amidoamine as biocide or bioresistant additive. In other embodiments, the quenching compositions use the polyamidopolyamine compound and/or non-polymeric amidoamine as a lubricating additive. In another embodiment, the quenching compositions use the polyamidopolyamine compound and/or non-polymeric amidoamine compound for quenching properties and biocidal or bioresistant properties. In still other embodiments, the quenching compositions used the polyamidopolyamine and/or non-polymeric amidoamine compound to add quenching, biocidal/bioresistant, and anti-foaming, low foaming or defoaming properties and lubricating properties. When the non-polymeric amidoamine has no free amines, it is used for lubricating, anti-foaming and quenching purposes, not to impact bioresistance. Thus in quenching compositions as described herein the polyamidopolyamine and/or non-polymeric amidoamine compounds may take the place of 1, 2, or 3 components of a conventional quenching composition.

Other Components for Quenching Compositions

Still other embodiments of the quenching compositions containing an polyamidopolyamine or non-polymeric amidoamine described herein also contain other components. Thus other additional components of the final use compositions comprising the polyamidopolyamines and/or non-polymeric amidoamines described herein include one or any combination of additional agents, including but not limited to, coalescing/drying agent, rheology modifier, ester, carboxylic acid, fatty acid, emulsifier, amine, thickener, lubricant, dispersant, antioxidant, alkaline compound, builder, solvent, amphipathic agent, carrier, preservative, buffer, metal deactivator, dye, fragrance, caustic agent, wetting agent, sequestering agent, fungicide, defoamer, antioxidant, die release fluid, antiwear agent, viscosity modifier, deemulsifier, natural triglyceride, animal fat, vegetable oil, fatty acid ester, and/or a phosphate ester. Still other optional components may be included in the concentrate and/or composition and may be selected by those skilled in the art. These additional components include, but are not limited to, salts, buffers, pH adjustors, enzymes, surfactants, tackifying agents, scale inhibitors, catalysts, clay control agents, friction reducers, corrosion inhibitors, dispersants, flocculants, H2S scavengers, $CO_2$ scavengers, oxygen scavengers, lubricants, gelling agent, crosslinking agent, wetting agents, relative permeability modifiers, resins, adhesives, and coating enhancement agents.

In one embodiment, such other components include other known quenching polymers used in conjunction with the polyamidopolyamine and/or non-polymeric amidoamine compound as an additional quenching component.

Suitable polymers useful in the aqueous quenchants and methods described herein are known in the art. Suitable polymers include polyvinyl alcohol; polyalkylene glycol (PAG); sodium polyacrylate (ACR); polyvinyl pyrrolidone (PVP); polyethyloxazoline (PEOX); and hybrid polymer quenchants. See, e.g., Eshraghi-Kakhki et al, International Journal of ISSI, 6(1):34-8 (2009). Other suitable polymers include, for example, those described in U.S. Pat. No. 3,220,893, which discusses a quenching medium containing an oxyalkylene polymer having oxyethylene and higher oxyalkylene groups which form a desirable covering over the metal substrate surface during quenching. The polymer layer that coats the metal permits relatively short quenching times, thereby resulting in minimum internal stress of the metal substrate, minimum distortion of the metal substrate, and imparts uniform hardenability of the metal substrate.

Another suitable aqueous quenching media is described in US Patent Publication No. 2009/0095384 which contains a polyvinylpyrrolidone/polyvinylcaprolactam copolymer; and a non-ionic, water-soluble or water-dispersible polymer including one or more of (a) a substituted oxazoline polymer; (b) a poly(oxyethyleneoxyalkylene) glycol polymer; or (c) a polyvinylpyrrolidone polymer.

Further, U.S. Pat. Nos. 3,902,929, 4,826,545, and RE 34119 discuss aqueous quenching media containing a polyvinylpyrrolidone and U.S. Pat. No. 4,087,290 discusses an aqueous quenching medium containing a water-soluble polyacrylate, such as a sodium polyacrylate, which forms a vapor blanket about the metal substrate during the quenching operation.

Suitable quenchants are known under various proprietary names, including, without limitation, AQUA-QUENCH® 140 (Houghton Int'l); AQUA-QUENCH® 145 (Houghton Int'l); AQUA-QUENCH® 245 (Houghton Int'l); AQUA-QUENCH® 251 (Houghton Int'l); AQUA-QUENCH® 260 (Houghton Int'l); AQUA-QUENCH® 3699 (Houghton Int'l); AQUA-QUENCH® C (Houghton Int'l); PARQUENCH®60 and PARQUENCH®90; POLYQUENCH® 10, POLYQUENCH® 15, and POLYQUENCH® 20; PLASTIQUENCH™; and SPEED QUENCH™ 1 (all Park Metallurgical Corporation); AQUATENSID® (Petrofer); and the UCON™ (DOW Chemical Company) series of quenchants. Other suitable quenchants are known in the art.

In certain embodiments, the aqueous quenching fluid comprises capped polyalkylene glycols, polyvinylpyrrolidone (PVP), polyvinylpyrrolidone copolymers, polyethyloxazoline (PEOX), polyethyloxazoline copolymers, polyacrylate, polyacrylate copolymers, or mixtures thereof. In certain other embodiments, the aqueous quenching fluid comprises uncapped polyalkylene glycols, polyvinylpyrrolidone (PVP), polyvinylpyrrolidone copolymers, polyethyloxazoline (PEOX), polyethyloxazoline copolymers, polyacrylate, polyacrylate copolymers, or mixtures thereof. In still other embodiments, the aqueous quenching fluid comprises capped and uncapped polymers, such as combinations of those identified herein. In one embodiment, the aqueous quenching fluid (bath and/or spray) comprises polyalkylene glycol (e.g., Houghton Aqua Quench® 365). In another embodiment, the aqueous quenching fluid (bath and/or spray) comprises a polyvinylpyrrolidone (PVP) polymer (e.g., Houghton Aqua Quench® C). In another embodiment, the aqueous quenching fluid (bath and/or spray) comprises a PEOX polymer (e.g., Houghton Aqua Quench® 3600). In still another embodiment, the aqueous quenching fluid (bath and/or spray) comprises PVP/PVC, vinylpyrrolidone/vinyl caprolactam copolymer (e.g., Houghton Aqua Quench® 4000).

In still another embodiment, the quenching fluid (bath and/or spray) one or more additional components include a carrier. In one example, the carrier is water. The carrier may be included in the quenching medium, thereby permitting use of the product by the customer without addition of further carrier. Alternatively, the carrier is present in the quenching medium in sufficient amounts to provide a stable solution for further dilution by the customer prior to use. The carrier may also be added by the customer to a concentrated quenching medium composition prior to use. However, more water made be added to the composition to ensure that the final quenching medium contains sufficient water for use by the customer.

Addition components with antimicrobial activity in addition to that activity provides by the polymeric polyamidopolyamines or non-polymeric amideamines may optionally be added to the quenching baths or sprays used in the processes described herein to prevent or reduce the accumulation of microorganisms in the system. The particular antimicrobial selected will depend on the process parameters, including aqueous quenching fluid, hydraulic fluid, the metal or metal alloy, the dimensions of the metal or metal substrate being quenched, among others. Such components include, for example biocides, bactericides or fungicides, e.g. polyaminopropylbiguanide (obtainable from Arch under the trade name CosmocilCQ™), paraformaldehyde, glutaraldehyde, phenoxyethanol, 2,4-dichlorobenzyl alcohol, 2,3-dibromo-3-nitrilopropionamide, and 5-chloro-2-methyl-2H-isothiozol-3-one. Suitable biocides are known in the art, including, without limitation, CONTRAM™ biocides (Lubrizol); the BIOBAN™, DOWICIDE™ KATHON™, ROCIMA™ and KORDEK™ brand biocides (Dow Chemical); MERGAL® brand biocides (ECT CV Corp.); TROY-SHIELD® (Troy Technical Corp) (iodopropynyl butylcarbamate). One of skill in the art would be able to make such a selection, taking into consideration the teachings of this specification. In one embodiment, the antimicrobial is the Grotan® reagent (Troy Corporation). In another embodiment, the antimicrobial may be selected from the list of microbicides discussed in the catalog "Metalworking", Buckman Laboratories, Inc., 2010, which is herein incorporated by reference in its entirety. In a further embodiment, the antimicrobial is the Busan® 1060 reagent (Buckman Laboratories). Other examples of suitable antimicrobials are the KATHON™ 886 MW product and KATHON™ 893 MW product (Dow Chemical Company). Other suitable biocides may be readily determined by one of skill in the art.

Still additional components include preservatives and also further compounds such as ethanolamine, polyalkylene oxides, polyethylene glycols. ethanol amine or amine soaps, buffer, metal deactivator, dye, fragrance, caustic agent, wetting agent, sequestering agent, among others.

Conventional antifoams/defoamers include components such as silicone oils, fatty alcohol alkoxylates, alcohol alkoxylates, carboxylic esters or phosphoric esters. Suitable antifoam agents are known in the art, including, without limitation, the TEGO® brand antifoams (Evonik Industries); XIAMETER® brand antifoams (Dow Corning); SAF-115, SAF-125, SAF-150, SAF-151, SAF-250, SAF-251 (Silchem Inc.); SURTECH® antifoams (PMC Crystal); Additive 2901 (Quaker Chem); and TROYKYD® brand defoamers (Troy Technical Corp). Other suitable antifoams can be readily determined by one of skill in the art.

"Antioxidants" as described herein are useful additives for preventing the degradation of the hydraulic fluid or quenching bath or quenching spray through oxidation. Such antioxidants may be selected from among an aromatic amine, quinoline, and phenolic compounds. In one embodiment, the antioxidant is an alkylated diphenyl amine (Vanlube® NA reagent, polymerized trimethyl-dihydro-quinoline (Vanlube® RD reagent) or 4,4'-methylene bis(2,6-di-tert-butylphenol).

"Corrosion inhibitors" may be selected from the battery of conventional corrosion inhibitors for both ferrous and non-ferrous metals used in the industry. In one embodiment, the corrosion inhibitor is tolyltriazole. Another corrosion inhibitor is sodium nitrite, borax, amines, ammonium salts of organic acids, phosphoric esters, alcohol alkoxylates, or 2-butyne-1,4-diol. However, other known and commercially available corrosion inhibitors could readily be used by one of skill in the art, taking into consideration the teachings of this specification.

"De-emulsifiers" as described herein may also optionally be included in the quenching baths or quenching sprays utilized herein. This is particularly useful when high agitation rates are utilized during the process. However, their inclusion is not required. One of skill in the art would be able to select a suitable de-emulsifier for use herein, taking into consideration the teachings of this specification.

These "additional" components may be present in the composition at about 0.05% to up to about 20% by weight. In one example, these components are present in combination in the quenching compositions at about 0.05, 0.1, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% by weight, or fractional percentages therebetween.

In one exemplary embodiment, a metal quenching media therefore advantageously comprises 60 to 99.8% by weight of water as carrier, 0.5 to 40% polyamidopolyamine or non-polymeric amidoamine, and 0.1 to 20% by weight of customary additives. In still another example, an aqueous quenching medium contains a polyamidopolyamine having a weight average molecular weight of about 10,000 in a concentration of about 25% to about 35% by weight and 55% water. The aqueous quenching medium may also contain about 0.05% to about 10% by weight of additives, including, without limitation, corrosion inhibitors and defoamers.

Concentrates of the Quenching Medium

The invention also provides a concentrate which contains the polyamidopolyamine and/or non-polymeric amidoamine components described above. This concentrate may be utilized by those skilled in the art for preparing an aqueous quenching medium useful in the heat treatment of metal substrates. In one example, the concentrate contains water and at least about 0.5% by weight of a polyamidopolyamine and/or non-polymeric amidoamine described above. In another example, the concentrate contains water and about 0.5% to 40% by weight of these polyamidopolyamine and/or non-polymeric amidoamines. In a further example, the concentrate contains about 5% to about 20% of these polyamidopolyamine and/or non-polymeric amidoamines described above.

Methods of Use of these Compositions

Various methods of heat treating metal substrates are known and include heating a metal substrate to an elevated temperature and then cooling. The cooling step, which is known in the art as "quenching", typically is performed rapidly and is accomplished by either immersion quenching or spray quenching. Immersion quenching involves immersing the hot metal substrate in a liquid quenching medium, i.e. a quenching bath. Spray quenching involves spraying quenchant on the heated metal part as it travels through a quench barrel or quench ring. The process of quenching involves the use of certain hydraulic equipment, which requires hydraulic fluids for performance. These quenching systems typically use large amounts of both aqueous quenchant and hydraulic fluid. The amount of quenchant used can be sizable depending upon the size of the metal product that is being quenched.

Thus the polyamidopolyamine and non-polymeric amidoamines compositions described herein can also be used in compatible fluids, e.g. hydraulic fluids. Such compatibility is important in circumstances in which these fluids contaminate each other during use.

In one embodiment, a process for increasing the efficiency of a metal quenching bath comprises the following steps, including providing in a container or quenching tank a metal quenching bath comprising a polyamidopolyamine and/or non-polymeric amidoamine as described herein. Generally, metal or metal substrates enter the quenching bath at temperatures as high as 1600° C. While the bath is being used for quenching, the bath temperature is kept about 100° F. and 120° F. (i.e., 37.7° C. and 48.9° C.) to keep the quenching fluid at its desired quenching temperature.

In one embodiment, a process for increasing the efficiency of a metal spray quenching, comprises the following steps, including spraying a metal substrate with a quenching fluid containing a polyamidopolyamine and/or non-polymeric amidoamine as described herein. Generally, metal or metal substrates enter the quenching ring or quench barrel at temperatures as high as 1600° C. While the spray is being used for quenching, the spray temperature is kept between about 100° F. and 120° F. (i.e., 37.7° C. and 48.9° C.) to keep the quenching fluid at its desired quenching temperature.

The processes of the present invention are performed using conventional metal quenching bath equipment or quenching spray equipment. One of skill in the art would readily be able to select suitable quenching equipment for use in quenching the selected metal, taking into consideration the teachings of this specification.

When used in a quenching composition, it is anticipated that the compositions comprising the polyamidopolyamines will be used at a concentration of between about 10 to about 30% by weight of the resulting use composition, and can replace or work in tandem with another quenchant, while also replacing one or more typical quenching additives for lubricity, bio resistance and/or form control. Compositions containing non-polymeric amidoamines are anticipated to work with the polyamidopolyamines in this context, or as additives to other known quenchant formulations. See, for example, U.S. Pat. Nos. 8,764,914; 4,486,246; 4,528,044; 4,381,205; and 4,404,044 which describe some examples of known quenching fluids.

In another aspect, a method of altering surface behavior of a liquid is provided. Form, pockets of air that are entrapped in a liquid, is often present in coolants and processing liquids and causes problems. Form can negatively influence the cooling efficiency or lubrication properties of the metalworking fluid and limits the visual inspection of the working process. Further problems include reduction of pump efficiency; reduced capacity of pumps and storage tanks; bacterial growth; dirt flotation/deposit formation; reduced effectiveness of the fluid; and downtime to clean tanks. In one embodiment, the liquid is an aqueous quenching medium. In one embodiment, the method includes adding to the liquid the polyamidopolyamine and/or non-polymeric amidoamine compound described above. The present invention includes the use of the polyamidopolyamine and/or non-polymeric amidoamine for altering surface behavior, e.g., for use as an anti-foam, defoam or low-foaming agent, and/or deaeration agent. In one embodiment, polyamidopolyamine and/or non-polymeric amidoamine is added to an aqueous quenching medium as an anti-foam agent. The polyamidopolyamine and/or non-polymeric amidoamine compound described herein can be used alone as an antifoam or low foam component in the compositions or in conjunction with another antifoam agent.

In another aspect, a method of providing antimicrobial or bioresistant properties to a metalworking fluid is provided. In one embodiment, the method includes adding a described polyamidopolyamine to the metalworking fluid. In another embodiment, the method includes adding a non-polymeric amidoamine to the metalworking fluid. In another embodiment, a mixture of these compounds can be added for enhance bioresistance in a quenching fluid. In one embodiment, the metalworking fluid is an aqueous quenchant. If left untreated, dangerous microorganisms are inevitable in aqueous metalworking fluids due to the water content, elevated temperatures, and contaminants. Good maintenance of metalworking fluid re-circulation systems can extend the lifetime of coolants and ensure the quality of the tools produced. In metalworking fluids, as in the other water-based environments, microorganisms usually live in the form of biofilms, the communities of bacteria and fungi attached to the surface of sumps, metal parts and also to each other. Biofilms exhibit very high resistance to biocides.

In one embodiment a described polyamidopolyamine can be used alone as an antimicrobial or bioresistant or in conjunction with one or more antimicrobial or bioresistant agents in a heat treating, e.g., quenching composition. In another embodiment, a described non-polymeric amidoamine can be used alone as a antimicrobial or bioresistant or in conjunction with one or more antimicrobial or bioresistant agents in these compositions. Non-polymeric amidoamine and polyamidopolyamine can be used together or in conjunction with one or more antimicrobial or bioresistant agents. In addition, polyamidopolyamine and/or non-polymeric amidoamine may also be used in conjunction with other anti-microbial techniques, such as the use of uv light or ozonation.

When employed as an additive to other known heat treating compositions, e.g., quenchants, it is anticipated that the present polyamidopolyamine and/or non-polymeric amidoamine—containing compositions will replace multiple components currently in use. In one embodiment, a composition described herein can be used simultaneously for its characteristics as both a lubricant and a defoamer, thereby replacing two components with a single component. Similarly, a composition described herein which has bioresistance or antimicrobial characteristics, as well as defoaming and/or lubricity characteristics may replace three other components in a suitable composition.

In general, when use as a defoamer, the polyamidopolyamines and/or non-polymeric amidoamines and/or compositions containing them can desirably replace silicone defoamers. It is anticipated that as a defoamer additive, the compositions or the compounds isolated therefrom may be use at a concentration of between about 0.1 to 0.5% by weight of the resulting use composition, e.g., metal working fluid. This range includes fractional numbers and the endpoints in the range, e.g., the present polyamidopolyamine and/or non-polymeric amidoamine—containing compositions can be added at e.g., 0.1, 0.2, 0.3, 0.4 and 0.5% by weight of the resulting use composition.

When used primarily as an additive for its anti-microbial/bioresistant characteristics, it is anticipated that the compositions comprising the polyamidopolyamines and/or non-polymeric amidoamines will be used at a concentration of between about 1 to about 3% by weight of the resulting use composition, e.g., a paint or polyurethane coating fluid. This range includes fractional numbers and the endpoints in the range, e.g., the present polyamidopolyamine compositions can be added at e.g., 1.0, 1.3, 1.5, 1.7, 2.0, 2.2, 2.4, 2.6, 2.7, and 3.0% by weight of the resulting use composition. Most desirably, the compositions can be used as a formaldehyde-free anti-microbial.

When used primarily as an additive for its lubricant characteristics and optionally its bioresistant/antimicrobial characteristics, it is anticipated that the compositions comprising the polyamidopolyamines and/or non-polymeric amidoamines will be used at a concentration of between about 5 to about 30% by weight of the resulting use composition, e.g., a lubricating fluid that does not degrade in the presence of a microorganism. This range includes fractional numbers and the endpoints in the range, e.g., the present polyamidopolyamine compositions can be added at e.g., 5.0, 5.5, 6.0, 6.5, 7.0, 8.0, 9.0, 10, 11, 12, 13, 14, 15, 16, 17, 18, 19, 20, 21, 22, 23, 24, 25, 26, 27, 28, 29 and 30% by weight of the resulting use composition.

Use of the multi-functional polyamidopolyamine and/or non-polymeric amidoamines to replace multiple other components of a quenching fluid reduces the quenching costs for the customer, and produces less waste.

EMBODIMENTS

One embodiment is a metal quenching composition comprising (a) a component comprising at least one of: i. a polyamidopolyamine compound having a molecular weight of about 500 to about 100,000 and comprising a pendant amino group; or ii. a non-polymeric amidoamine having a molecular weight of about 290 to about 5000 and comprising an amino group; and (b) a hydroxyl containing diluent. In another embodiment this composition comprises about 0.5 to about 40% of component (a). In another embodiment, these compositions further comprises a quenchant.

In some embodiments of these compositions the hydroxyl containing diluent is water. In other embodiments, the hydroxyl containing diluent is an organic diluent. The hydroxyl containing diluent, in one embodiment comprises an alcohol, glycol, polyalkylene glycol, polyol, carbitol, cellosolve, or combinations thereof. In other embodiments, the hydroxyl containing diluent comprises triethanolamine, ethylene glycol, diethylene glycol, N,N,N',N'-tetrakis(2-hydroxypropyl)ethylenediamine, glycerin, or combinations thereof.

In other embodiments, the polyamidopolyamine used in the above-described composition is water-soluble or water dispersible. Alternatively or additionally, the quenchant composition further comprises a water soluble acid to enhance water solubility. In some embodiments, the water soluble acid is phosphoric acid, acetic acid, glycolic acid, lactic acid, or combinations thereof.

In other embodiments, the polyamidopolyamine in these compositions has a cloud point in water of about 180° F. or less. In other embodiments, the polyamidopolyamine in these compositions has low-foaming, non-foaming, or defoaming properties. In still other embodiments, the polyamidopolyamine used in these compositions is non-shearing in water.

In some of these various embodiments, the polyamidopolyamine is a condensation product of one or more polyamine comprising at least 3 amino groups with one or more $C_2$ to $C_{18}$ polybasic acid or derivative thereof. In other embodiments, the polyamidopolyamine is a condensation product of 2 polyamines comprising at least 3 amino groups with one or more $C_4$ to $C_{16}$ polybasic acid or derivative thereof. In still other embodiments, the polyamidopolyamine is a condensation product of one or more polyamines comprising at least 3 amino groups with two $C_4$ to $C_{16}$ polybasic acid or derivative thereof. In still other embodiments, the polyamidopolyamine is a condensation product of one polyamine comprising at least 3 amino groups with one polyamine comprising 2 amino groups, and one or more $C_4$ to $C_{16}$ polybasic acid or derivative thereof. The polybasic acid derivative used in these condensation reactions can be as described previously herein.

In still other embodiments of the condensation reactions used to produce the polyamidopolyamines of the quenching compositions, the molecular weight of said polybasic acid is about 90 to about 300. In still other embodiments, the polybasic acid or derivative comprises at least 2 C(O)OH groups or ester, anhydride, acid halide, lactone, polyanhydride, or lactam reactive groups thereof.

In other embodiments, the polyamidopolyamine of the quenching composition is the reaction product of a condensation reaction that employs a hydroxyl-containing diluent comprising water and a mole ratio of said polyamine to polybasic acid in the condensation reactions discussed above is about 2 to 1. In other embodiments, the hydroxyl-containing diluent lacks water and the mole ratio of said polyamine to polybasic acid is from about 1:1 to about 2:1, including all fractional numbers therebetween.

In still other embodiments, the polyamidopolyamine is produced by a condensation reaction using the polyamine triaminononane. In another embodiment, the polyamidopolyamine is produced by a condensation reaction using one or more polyamines of the forulae:

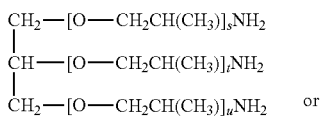

or

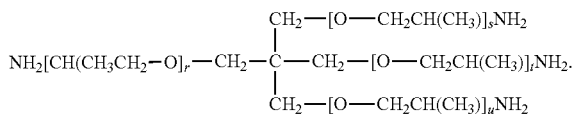

as described above.

In another embodiment, the polyamidopolyamine in the quenching composition has Formula I of FIG. 6A, wherein x, y, and z are additively a number between 3 to about 90, including the endpoints in the range; wherein x', y', z' are additively a number between 3 to about 90, including the endpoints in the range; and wherein a, b, and c are additively a number between 3 to about 90, including the endpoints in the range.

In another embodiment, the polyamidopolyamine in the quenching composition has Formula II of FIG. 6B, wherein x, y, and z are additively a number between 3 to about 90, including the endpoints in the range; and wherein x', y', z' are additively a number between 3 to about 90, including the endpoints in the range.

In another embodiment, the polyamidopolyamine in the quenching composition has Formula III of FIG. 6C, wherein x, y, and z are additively a number between 3 to about 90, including the endpoints in the range; wherein x', y', z' are additively a number between 3 to about 90, including the endpoints in the range; and wherein a, b, and c are additively a number between 3 to about 90, including the endpoints in the range.

In another embodiment, the polyamidopolyamine in the quenching composition has Formula IV of FIG. 7A, wherein x, y, and z are additively a number between 3 to about 90, including the endpoints in the range; wherein x', y', z' are additively a number between 3 to about 90, including the endpoints in the range; and wherein a, b, and c are additively a number between 3 to about 90, including the endpoints in the range.

In another embodiment, the polyamidopolyamine in the quenching composition has Formula V of FIG. 7B, wherein x, y, and z are additively a number between 3 to about 90, including the endpoints in the range; wherein x', y', z' are additively a number between 3 to about 90, including the endpoints in the range; and wherein a, b, and c are additively a number between 3 to about 90, including the endpoints in the range.

In another embodiment, the quenching composition contains a non-polymeric amidoamine, which is a condensation product of i. one or more primary amine comprising at least 2 amino groups and one or more $C_2$ to $C_{18}$ monobasic acid or derivative thereof; or ii. two or more primary amines comprising at least 2 amino groups and one or more $C_2$ to $C_{18}$ monobasic acid or derivative thereof; or iii. one or more primary amines comprising at least 2 amino groups and two $C_2$ to $C_{18}$ monobasic acid or derivative thereof; or iv. one primary amine comprising at least 2 amino groups, a second amine comprising 2 amino groups, and one or more $C_2$ to $C_{18}$ monobasic acid or derivative thereof. In these embodiments, the non-polymeric amidoamines comprises at least one non-reacted free amino group. In one such embodiment, the monobasic acid derivative used in the condensation reaction comprises an ester, anhydride, acid halide, lactone, polyanhydride, or lactam thereof. The monobasic acid is selected from one of those previously identified herein. In another embodiment, the molecular weight of said monobasic acid is about 46 to about 312. In another embodiment, the monobasic acid or derivative used to prepare the non-polymeric amidoamine comprises a C(O)OH group or an ester, anhydride, acid halide, lactone, polyanhydride, or lactam reactive group thereof.

In another embodiment, the quenching composition contains a non-polymeric amidoamine of the formula

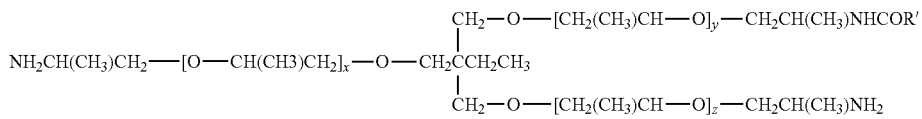

wherein x, y, and z are additively a number between 0 to about 87, including the endpoints in the range, and R' is $C_1$ to $C_{11}$ alkyl or $C_1$ to $C_{11}$ substituted alkyl.

In another embodiment, the quenching composition contains a non-polymeric amidoamine of the formula

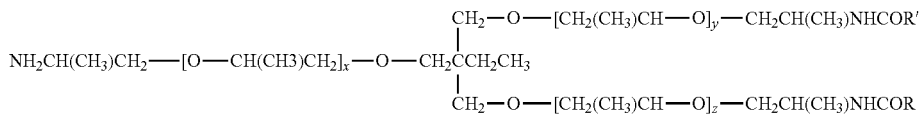

wherein x, y, and z are additively a number between 0 to about 87, including the endpoints in the range, and R and R' are independently $C_1$ to $C_{11}$ alkyl or $C_1$ to $C_{11}$ substituted alkyl.

In another embodiment, the quenching composition contains a non-polymeric amidoamine of the formula

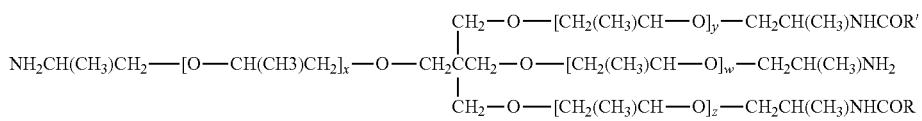

wherein w, x, y, and z are additively a number between 0 to about 86, including the endpoints in the range, and R and R' are independently $C_1$ to $C_{11}$ alkyl or $C_1$ to $C_{11}$ substituted alkyl.

In another embodiment, the quenching composition contains a non-polymeric amidoamine of the formula

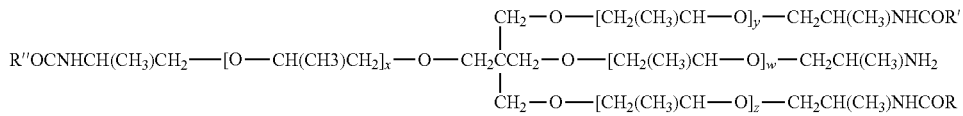

wherein w, x, y, and z are additively a number between 0 to about 86, including the endpoints in the range, and R, R" and R''' are independently $C_1$ to $C_{11}$ alkyl or $C_1$ to $C_{11}$ substituted alkyl.

In another embodiment, the quenching composition contains a non-polymeric amidoamine prepared by a condensation reaction in which the hydroxyl-containing diluent comprises water; the mole ratio of said primary polyamine to monobasic acid provides at least one free amino group, and the water is added at the end of the reaction. In another embodiment, such condensation reactions can convert all amino groups to amide, and the condensation products do not act as antagonists to microorganisms but retain defoaming and lubrication properties for use in the quenching composition. In yet another embodiment, the composition uses a non-polymeric amidoamines or polyamidopolyamine in which the hydroxyl-containing diluent lacks water and the mole ratio of said primary amine to monobasic acid provides at least one free amino group.

Among the primary amines used in the condensation reactions to produce a non-polymeric amidoamines are a primary diamine, primary triamine, primary tetraamine or a higher primary amine. For example, one condensation reaction employs an amine is of the formula

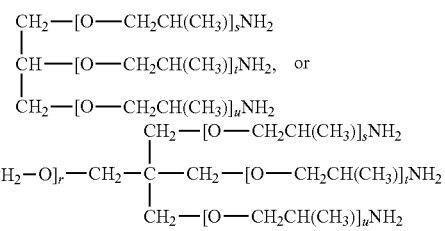

as described above.

The quenching compositions described herein in one embodiment can include an additional biocide. In other embodiments, the quenching compositions include one or more components including, without limitation, a coalescing/drying agent, rheology modifier, ester, carboxylic acid, fatty acid, emulsifier, amine, thickener, lubricant, dispersant, antioxidant, alkaline compound, builder, solvent, amphipathic agent, carrier, biocide, preservative, buffer, metal deactivator, dye, fragrance, caustic agent, wetting agent, sequestering agent, fungicide, defoamer, antioxidant, die release fluid, corrosion inhibitor, antiwear agent, viscosity modifier, de-emulsifier, natural triglyceride, animal fat, vegetable oil, fatty acid ester, phosphate ester, or combinations thereof.

Such quenching compositions include may be characterized by a cloud point of about 25 to about 82° C. or 77° F. to about 180° F. In another embodiment, the quenching has one or more properties selected from biocidal properties, bioresistant properties or defoaming properties. In other embodiments, the quenching composition, which has a pH of about 8 to about 11. In still a further embodiment, compatible compositions such as hydraulic fluids are designed to contain the same or similar polyamidopolyamines or non-polymeric amidoamines as described herein, in the event that there is some inadvertent admixture of the hydraulic fluids or other fluids used in the quenching methods described herein.

Methods for quenching a metal, said method comprising immersing or spraying a heated metal with any of the quenching compositions disclosed herein including any of the specific embodiments described in this specification.

EXAMPLES

The following examples are illustrative only and are not intended to be a limitation on the present invention.

Example 1

Polyamidopolyamine and Characteristics

Polyamidopolyamine 3587-203 is a condensation reaction product of Huntsman Jeffamine T-403 (5 moles) and adipic acid (4 moles). The polyamidopolyamine was evaluated by gel permeation chromatography analysis (GPC) and/or characterized as a diacid amide product by NMR and MALDI mass spectrometry.

Polyamidopolyamine 3587-185 is a condensation reaction product of Huntsman Jeffamine T-403 (5 moles) and adipic acid (4 moles). The reaction was run in dipropylene glycol solvent, 50% of the charge. The polyamidopolyamine was characterized as a diacid product by NMR and MALDI mass spectrometry.

Polyamidopolyamine 3533-85 is a condensation reaction product of Huntsman Jeffamine T-403 (2 moles) and adipic acid (1 moles). The polyamidopolyamine was characterized as a diacid amide product by NMR and MALDI mass spectrometry and by gel permeation analysis (GPC).

The following Table 1 compares the characteristics of these polyamidopolyamines:

TABLE 1

| Semi-quantitation distribution by MALDI-TOF | Mole % 3587-203 | Mole % 3587-185[1] | Mole % 3533-85 |
|---|---|---|---|
| Unreacted T-403 Condensation Products | 43.9 | 64.6 | 51 |
| One T-403 + one adipic | 15.3 | 18.2 | 0 |
| Two T403 + one adipic | 18.4 | 13.8 | 29 |

TABLE 1-continued

| Semi-quantitation distribution by MALDI-TOF | Mole % 3587-203 | Mole % 3587-185[1] | Mole % 3533-85 |
|---|---|---|---|
| Three T403 + two adipic | 12.9 | 2.6 | 12 |
| Four T403 + three adipic | 9.5 | 0.8 | 5 |
| Five T403 + four adipic | | | detected |
| Mole Ratio: T403/adipic | 5:4 | 5:4 | 2:1 |
| Avg MW measured by GPC | 6,240 | — | 2,240 |
| Avg MW measured by MALDI-TOF | 858 | 577 | 1,220 |

[1]Reaction run in in dipropylene glycol

The GPC measurement according to Organization for Economic Cooperation and Development Test 118 (OECD 118) appears more accurate in determining molecular weight for these compositions. The MALDI-TOF is semi-quantitative for product distribution.

Approximate calculated weight % of polyamidopolyamine and unreacted Huntsman T403 from the condensation reactions: A MW of 440 daltons was used for Huntsman T403; GPC data was used to determine the average MW of the polyamidopolyamines. Weight % were calculated from the mole % determined from the same quantitative MALDI-TOF analysis. Results are as shown in Table 2.

TABLE 2

| | Condensation reaction product: | |
|---|---|---|
| | 3587-203 | 3533-85 |
| Mole ratio T403/adipic | 5/4 | 2/1 |
| Avg MW of polyamidopolyamine by GPC | 6,240 | 2,240 |
| Wt % unreacted T403 | 5.2 | 17 |
| Wt % of polyamidopolyamine | 94.8 | 83 |

Example 2

Bioresistant Characteristics

Procedure: The test was run separately for bacteria and fungus. The bacteria inoculum was a mixed culture grown on Houghton fluids. The fungus test was run with the species, *Aspergillus niger*. Samples were continuously stirred at room temperature for the duration of the test. All fluids were tested at 0.75% in DI water with pH adjusted to 9.3. Bacteria and fungi were counted as colony forming units/ml (CFU/ml).

Test Formulations:

30A (amide rxn): 0.75% by wt 3587-167 in water with pH adjusted to 9.3. 3587-167 is the condensation product using Huntsman T403 and glycolic acid at a 1:1 mole ratio. It has no cloud point.

30B (amide rxn): 0.75% 3587-173 in water, adjusted to pH 9.3. 3587-173 is the condensation product using Huntsman T403 and lactic acid at 1:1 mole ratio. It has a cloud point of 142° F. (61° C.), which helps in defoaming.

Results: The results presented are for comparative analysis only. Table 3 shows the results for bacteria. Tables 4 and 5 show the results for fungus. Different bacteria and fungus species may give different results. % FR means % fluid resistance.

TABLE 3

Bacteria

| | | | Inoculation: | | | |
|---|---|---|---|---|---|---|
| CFU/ml | CFU/ml | % FR | CFU/ml | % FR | CFU/ml | % FR |
| | | | Time since Inoculation: | | | |
| 0 min | 6 min | | 30 min | | 2 hr | |
| 30A 2 × 10$^6$ | 1.8 × 10$^6$ | 10.0 | 6.7 × 10$^5$ | 66.5 | 3.4 × 10$^5$ | 83.0 |
| 30B 2 × 10$^6$ | 1.3 × 10$^6$ | 35.0 | 3.9 × 10$^5$ | 80.5 | 0 | 100.0 |

TABLE 4

Fungus (part 1)

| | | Inoculation: | | |
|---|---|---|---|---|
| | CFU/ml | CFU/ml | % FR | CFU/ml | % FR |
| Time since Inoculation: | 0 min | 2 hrs | | 4 hrs | |
| Total Days: | 0 | 0 | | 0 | |
| 30A | 2.1 × 10$^5$ | 1.5 × 10$^5$ | 28.6 | 1.6 × 10$^6$ | 23.8 |
| 30B | 2.1 × 10$^5$ | 1.0 × 10$^5$ | 52.4 | 6.0 × 10$^4$ | 71.4 |

TABLE 5

Fungus (part 2)

| | | Inoculation: | | |
|---|---|---|---|---|
| | CFU/ml | % FR | CFU/ml | % FR |
| Time since Inoculation: | 8 hrs | | 24 hrs | |
| Total Days: | 0 | | 1 | |
| 30A | 3.0 × 10$^4$ | 85.7 | 80 | 100.0 |
| 30B | 3.0 × 10$^4$ | 85.7 | 40 | 100.0 |

Example 3

Quenching Metal Substrates Using Aqueous Quenching Media

Experiments are conducted to determine cooling times using quenching compositions containing a polyamidopolyamine or non-polymeric amidoamine as described herein. The IVF Quenchotest (The Swedish Institute of Production Engineering Research) is utilized and includes the IVF data acquisition/recording unit, test probe, probe handle and furnace. The test probe (600 mm in length and 12.5 mm diameter of the Inconel® 600 probe enclosing a type K thermocouple —NiCr/NiAl— with a diameter of 1.5 mm) complies with the specification for testing quenchants as established by the International Federation for the Heat Treatment of Materials (IFHT). The furnace thermostat controls the power supplied to the furnace through diode rectification and is operated without a controlled atmosphere. The furnace temperature is adjusted to about 1625° F. (885° C.).

In each run, the metal substrate is heated to a temperature of about 1571° F. (855° C.) to about 1600° F. (870° C.) and then immersed in 1.0 kilograms of an aqueous quenching media containing a polyamidopolyamine described above which are maintained at a temperature of about 100° F. (40° C.). Data acquisition begins when the test probe temperature of the aqueous quenching medium reaches about 1562° F. (849° C.) and is acquired for about 60 seconds, i.e., until the temperature reached about 300° F.

After data collection, cooling curves are obtained using the data collected using the various polyamidopolyamine mixtures. Cooling times are determined from the cooling curves during which the test specimens are cooled from 1562° F. (849° C.) to less than 203° F. (95° C.).

Results are shown in FIGS. 1-5.

FIG. 1 is a cooling curve showing the comparison of polyamidopolyamine reaction products with water and Aqua Quench 260 (AQ260). AQ 260 is a commercial product supplied by Houghton International to slow down the quenching effect of water. Product 3587-193 is a polyamidopolyamine, the reaction of Huntsman Jeffamine T403 (10 moles) with adipic acid (9 moles). The reaction is performed in approximately 44% dipropylene glycol (DPG). The DPG remains in the reaction mixture. Cloud point (1%) approximately 81° Fahrenheit. The cooling curve measurements were made using the IVF quenchometer. Table 6 shows the parameters of the test leading to the curves of FIG. 1.

TABLE 6

| PROPERTY | UNIT | 13% 260 1.IVF | 3587-193.2.IVF | WATER.IVF |
|---|---|---|---|---|
| Max cooling rate | C./s | 177.43 | 187.03 | 207.67 |
| Temp at Max Cooling Rate | C. | 663.89 | 624.54 | 619.47 |
| Temp at Start of Boiling | C. | 844.3 | 815.88 | 844.21 |
| Temp at Start of Convection | C. | 156.28 | 137.64 | 57.68 |
| Cooling Rate at 300 C. | C./s | 66.26 | 80.83 | 95.22 |
| Time to 600° C. | s | 2.34 | 3.6 | 1.83 |
| Time to 400° C. | s | 3.83 | 4.91 | 2.93 |
| Time to 200° C. | s | 7.25 | 7.81 | 5.31 |
| Theta 1 | C. | 844.36 | 815.19 | 843.97 |
| Theta 2 | C. | 287.89 | 237.26 | 250.31 |
| HP-IVF (oils) | | 2311.62 | 2565.11 | 3194.38 |
| HP-IVF (polymers) | | 1339.89 | 1603.51 | 1874.86 |

| OPERATION PARAMETERS | |
|---|---|
| Product Type | Various |
| Medium Temp | 26 |
| Medium concentration | Various |
| Agitation Rate (m/s) | Moderate |

Figure 2:
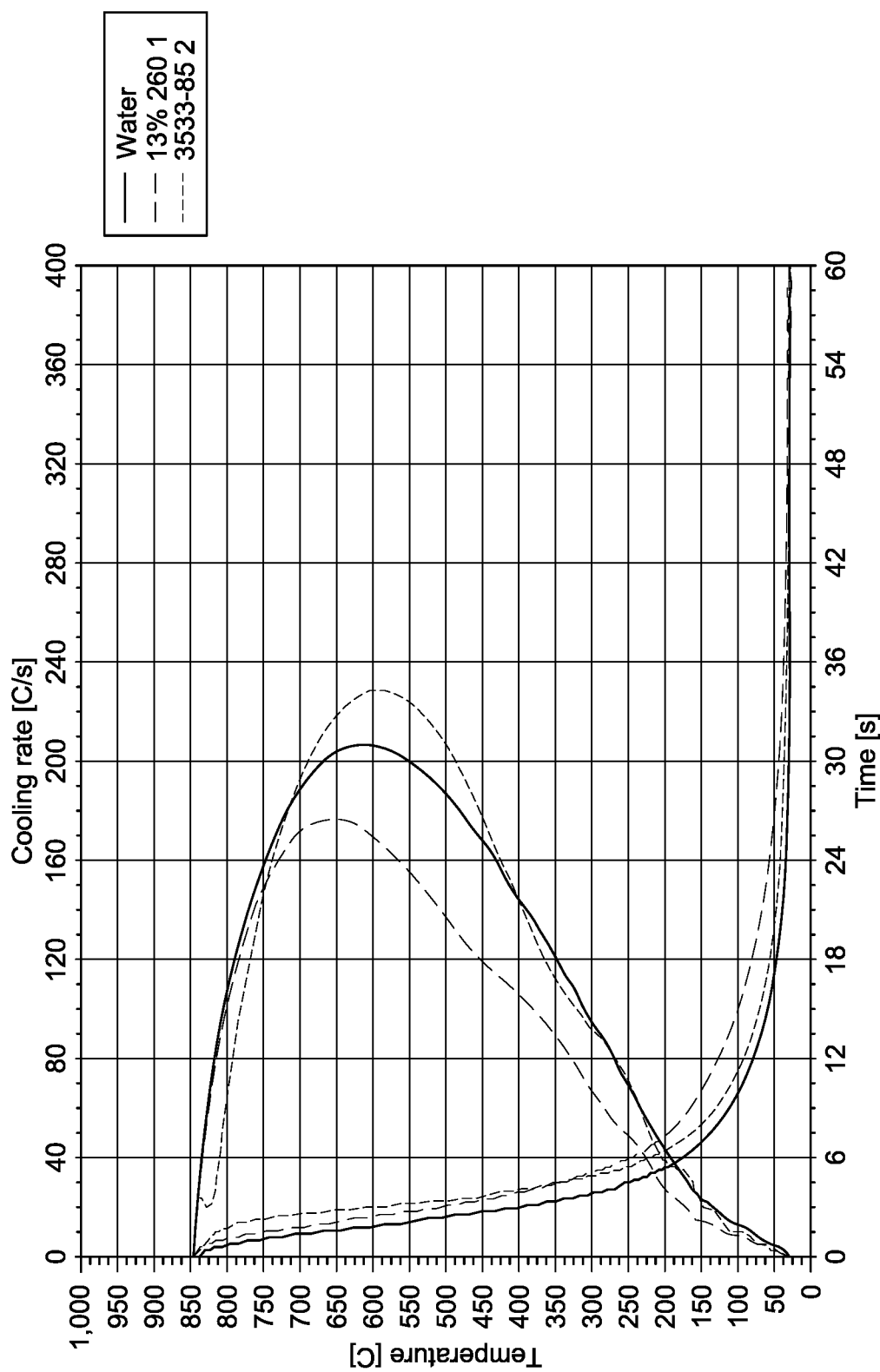
FIG. 2 shows the curves produced by the method described in FIG. 1 using product 3533-85-2 in the IVF method. 3533-85-2 is the product of a condensation reaction of Huntsman Jeffamine T 403 (2 moles) with adipic acid (1 mole). Cloud point (0.75%), approximately 86° F.; weight average molecular weight, 2,240; determined by GPC. The curves are water (solid line), 260-1 (a broken line) and 3533-85-2 (line of small dashes).

FIG. 2 shows similar curves produced using product 3533-85-2 in the IVF method. 3533-85-2 is the product of a condensation reaction of Huntsman Jeffamine T 403 (2 moles) with adipic acid (1 mole). Cloud point (0.75%), approximately 86° F.; weight average molecular weight, 2,240; determined by gel permeation column chromatography (GPC). Table 7 shows the parameters of the test leading to the curves of FIG. 2.

TABLE 7

| PROPERTY | UNIT | 13% 260 1.IVF | 3533-85 2.IVF | WATER.IVF |
|---|---|---|---|---|
| Max cooling rate | C./s | 177.43 | 229.23 | 207.67 |
| Temp at Max Cooling Rate | C. | 663.89 | 585.34 | 619.47 |
| Temp at Start of Boiling | C. | 844.3 | 824.16 | 844.21 |
| Temp at Start of Convection | C. | 156.28 | 139.13 | 57.68 |

TABLE 7-continued

| | | | | |
|---|---|---|---|---|
| Cooling Rate at 300 C. | C./s | 66.26 | 92.74 | 95.22 |
| Time to 600° C. | s | 2.34 | 3.03 | 1.83 |
| Time to 400° C. | s | 3.83 | 4.06 | 2.93 |
| Time to 200° C. | s | 7.25 | 6.51 | 5.31 |
| Theta 1 | C. | 844.36 | 823.02 | 843.97 |
| Theta 2 | C. | 287.89 | 226.32 | 250.31 |
| HP-IVF (oils) | | 2311.62 | 3097.66 | 3194.38 |
| HP-IVF (polymers) | | 1339.89 | 1868.75 | 1874.86 |

| OPERATION PARAMETERS | |
|---|---|
| Product Type | Various |
| Medium Temp | 26 |
| Medium concentration | Various |
| Agitation Rate (m/s) | Moderate |

Figure 3:
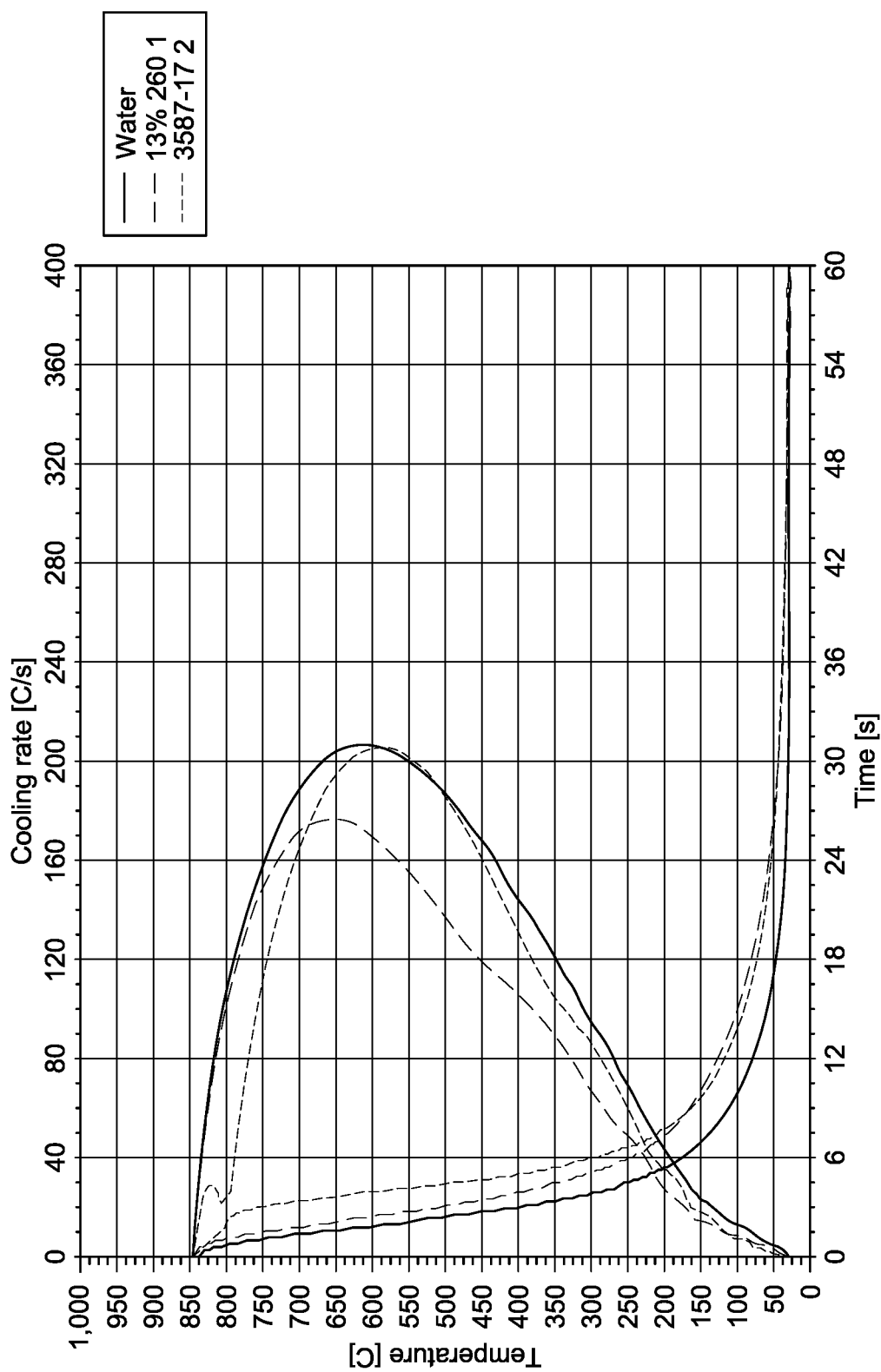
FIG. 3 shows the curves produced by the method described in FIG. 1 using product 3587-17-2 in the IVF method. 3587-17-2 is the product of a condensation reaction of Huntsman Jeffamine T 403 (2 moles) with azelaic acid. The reaction is run in 45% triethanolamine. The DPG and TEA are also used as solvents for the reactions and also form the intermediate ester which is then converted to amide, releasing that solvent. The triethanolamine remains in the reaction mixture. Cloud point 0.75%, approximately 75° F. The curves are water (solid line), 260-1 (a broken line) and 3587-17-2 (line of small dashes).

FIG. 3 shows the curves produced by the same method using product 3587-17-2 in the IVF method. 3587-17-2 is the product of a condensation reaction of Huntsman Jeffamine T 403 (2 moles) with azelaic acid. The reaction is run in 45% triethanolamine. The DPG and TEA are used as solvents for the reaction and also form the intermediate ester which is then converted to amido, releasing that solvent. The triethanolamme remains in the reaction mixture. Cloud point 0.75%, approximately 75° F. Table 8 shows the parameters of the test leading to the curves of FIG. 3.

TABLE 8

| PROPERTY | UNIT | 13% 260 1.IVF | 3587-17 2.IVF | WATER.IVF |
|---|---|---|---|---|
| Max cooling rate | C./s | 177.43 | 206.23 | 207.67 |
| Temp at Max Cooling Rate | C. | 663.89 | 594.26 | 619.47 |
| Temp at Start of Boiling | C. | 844.3 | 800.57 | 844.21 |
| Temp at Start of Convection | C. | 156.28 | 150.25 | 57.68 |
| Cooling Rate at 300 C. | C./s | 66.26 | 86.43 | 95.22 |
| Time to 600° C. | s | 2.34 | 3.94 | 1.83 |
| Time to 400° C. | s | 3.83 | 5.07 | 2.93 |
| Time to 200° C. | s | 7.25 | 7.81 | 5.31 |
| Theta 1 | C. | 844.36 | 800.35 | 843.97 |
| Theta 2 | C. | 287.89 | 222.32 | 250.31 |
| HP-IVF (oils) | | 2311.62 | 2782.5 | 3194.38 |
| HP-IVF (polymers) | | 1339.89 | 1724.5 | 1874.86 |

| OPERATION PARAMETERS | |
|---|---|
| Product Type | Various |
| Medium Temp | 26 |
| Medium concentration | Various |
| Agitation Rate (m/s) | Moderate |

Figure 4:
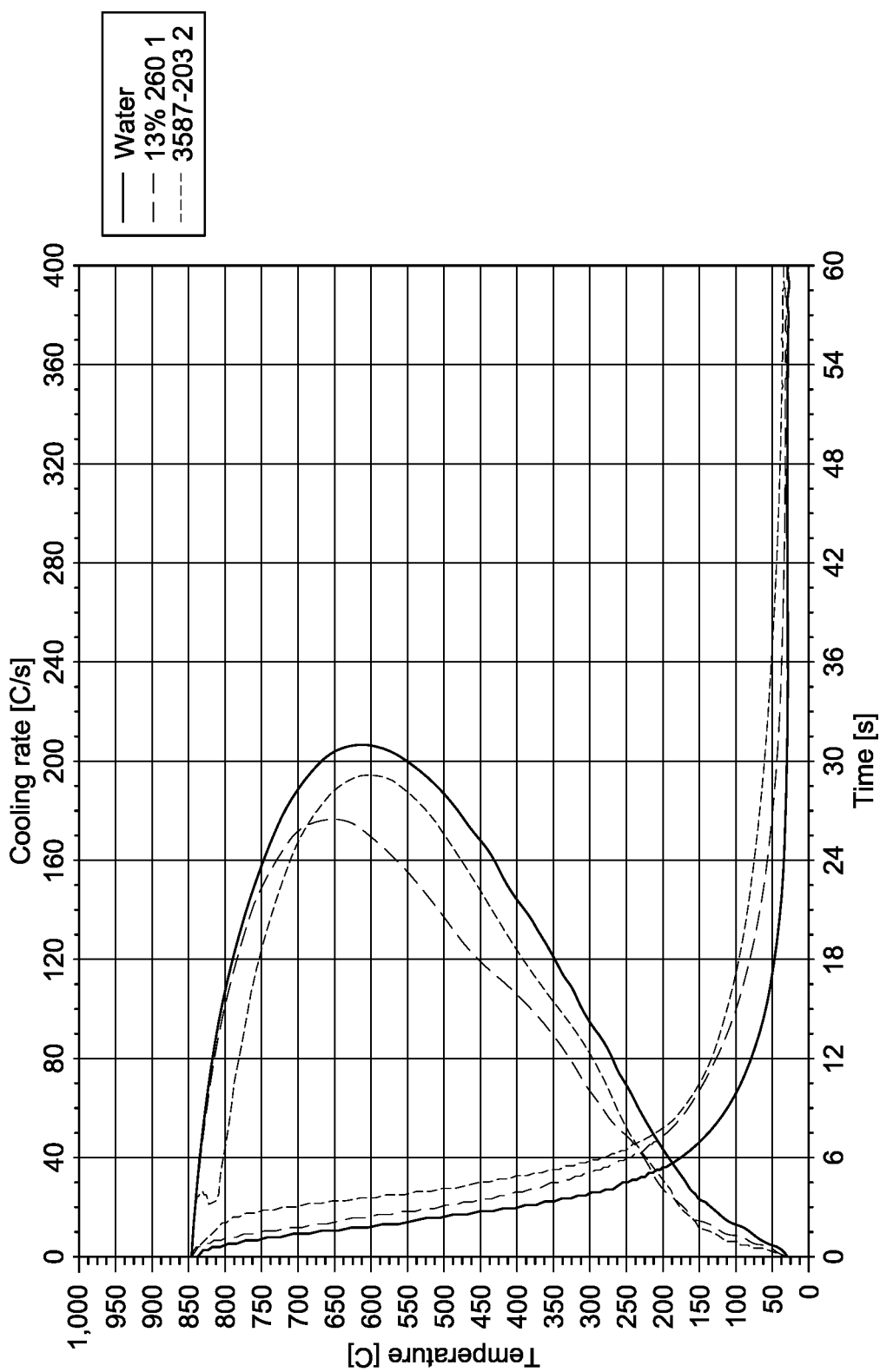
FIG. 4 shows the curves produced by the method described in FIG. 1 using product 3587-203-2 in the IVF method. 3587-203-2 is a product of the condensation reaction of Huntsman Jeffamine T 403 (5 moles) with adipic acid (4 moles). Cloud point was cloudy at ambient, about 70° F. but becomes clear on cooling. The average molecular weight by GPC is 6,240 daltons. The average molecular weight by GPC is 6,240 daltons. The curves are water (solid line), 260-1 (a broken line) and 3587-203-2 (line of small dashes).

FIG. 4 shows the curves produced by using product 3587-203-2 in the IVF method. 3587-203-2 is a product of the condensation reaction of Huntsman Jeffamine T 403 (5 moles) with adipic acid (4 moles). Cloud point was cloudy at ambient temperature and on cooling becomes clear. The MW (average) by GPC is 6,240 daltons. Table 9 shows the parameters of the test leading to the curves of FIG. 4.

TABLE 9

| PROPERTY | UNIT | 13% 260 1.IVF | 3587-203 2.IVF | WATER.IVF |
|---|---|---|---|---|
| Max cooling rate | C./s | 177.43 | 195.23 | 207.67 |
| Temp at Max Cooling Rate | C. | 663.89 | 600.15 | 619.47 |
| Temp at Start of Boiling | C. | 844.3 | 816.1 | 844.21 |
| Temp at Start of Convection | C. | 156.28 | 144.06 | 57.68 |
| Cooling Rate at 300 C. | C./s | 66.26 | 82.02 | 95.22 |
| Time to 600° C. | s | 2.34 | 3.47 | 1.83 |
| Time to 400° C. | s | 3.83 | 4.69 | 2.93 |
| Time to 200° C. | s | 7.25 | 7.69 | 5.31 |
| Theta 1 | C. | 844.36 | 814.56 | 843.97 |
| Theta 2 | C. | 287.89 | 237.98 | 250.31 |
| HP-IVF (oils) | | 2311.62 | 2677.11 | 3194.38 |
| HP-IVF (polymers) | | 1339.89 | 1647.1 | 1874.86 |

| OPERATION PARAMETERS | |
|---|---|
| Product Type | Various |
| Medium Temp | 26 |
| Medium concentration | Various |
| Agitation Rate (m/s) | Moderate |

Figure 5:
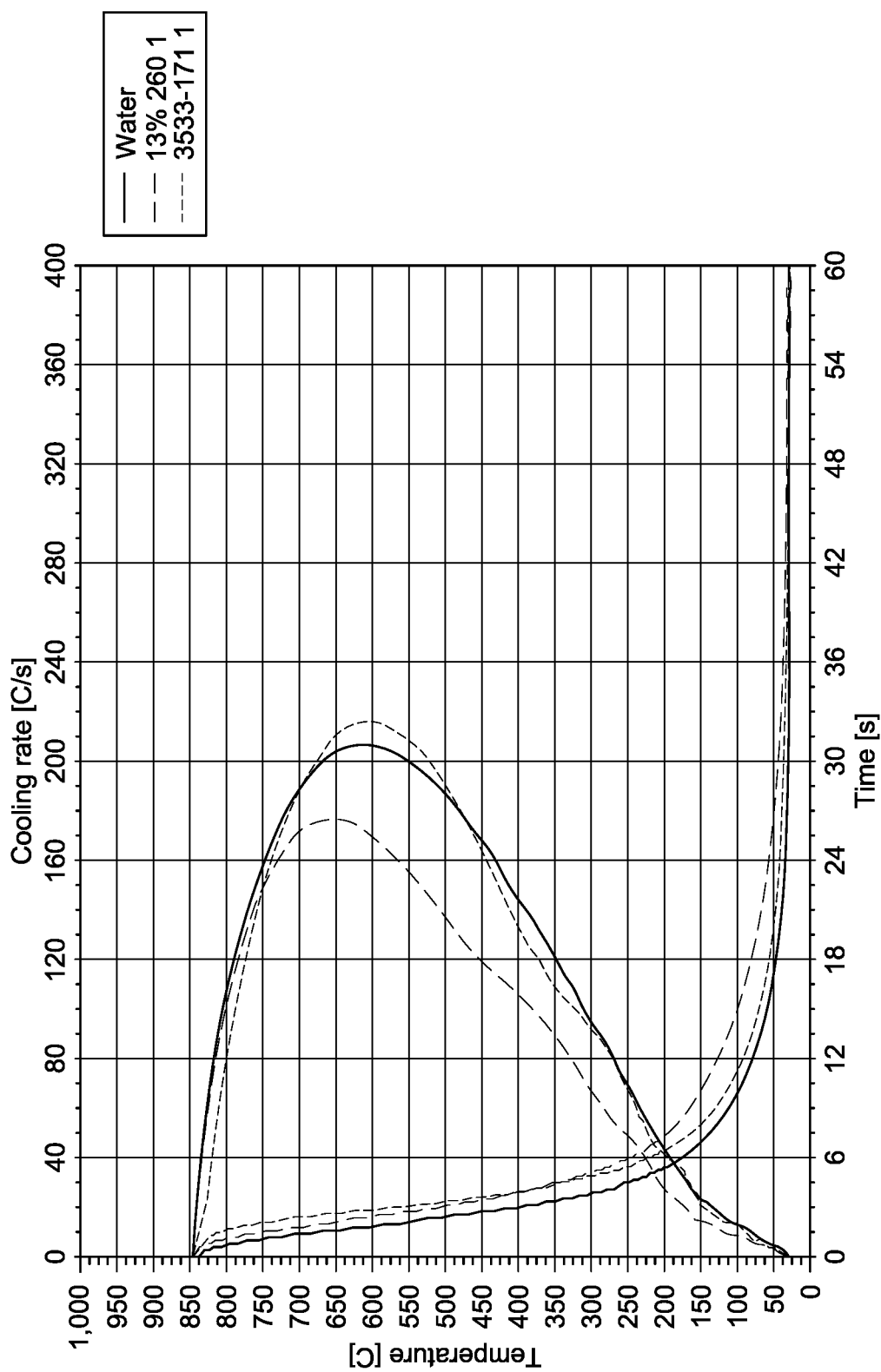
FIG. 5 shows the curves produced by the method described in FIG. 1 using product 3533-171-1 in the IVF method. 3533-171-1 is the product of the condensation reaction of Huntsman Jeffamine T 403 (2 moles) with adipic acid (1 mole) with about 12% water added when the reaction is cooled below 90° C. The water acts as a solvent to reduce the viscosity of the neat product to make it more flowable. Cloud point, about 88° F. The curves are water (solid line), 260-1 (a broken line) and 3533-171-1 (line of small dashes).

FIG. 5 shows the curves produced by using product 3533-171-1 in the IVF method. 3533-171-1 is the product of the condensation reaction of Huntsman Jeffamine T 403 (2 moles) with adipic acid (1 mole) with about 12% water added when the reaction is cooled below 90° C. The water acts as a solvent to reduce the viscosity of the neat product to make it more flowable. Cloud point, about 88° Fahrenheit. Table 10 shows the parameters of the test leading to the curves of FIG. 5.

TABLE 10

| PROPERTY | UNIT | 13% 260 1.IVF | 3533-171 1.IVF | WATER.IVF |
|---|---|---|---|---|
| Max cooling rate | C./s | 177.43 | 215.84 | 207.67 |
| Temp at Max Cooling Rate | C. | 663.89 | 595.46 | 619.47 |
| Temp at Start of Boiling | C. | 844.3 | 834.04 | 844.21 |
| Temp at Start of Convection | C. | 156.28 | 143.43 | 57.68 |
| Cooling Rate at 300 C. | C./s | 66.26 | 90.94 | 95.22 |
| Time to 600° C. | s | 2.34 | 2.7 | 1.83 |
| Time to 400° C. | s | 3.83 | 3.82 | 2.93 |
| Time to 200° C. | s | 7.25 | 6.38 | 5.31 |
| Theta 1 | C. | 844.36 | 832.65 | 843.97 |
| Theta 2 | C. | 287.89 | 238.26 | 250.31 |
| HP-IVF (oils) | | 2311.62 | 2922.34 | 3194.38 |
| HP-IVF (polymers) | | 1339.89 | 1795.53 | 1874.86 |

| OPERATION PARAMETERS | |
|---|---|
| Product Type | Various |
| Medium Temp | 26 |
| Medium concentration | Various |
| Agitation Rate (m/s) | Moderate |

Each and every patent, patent application, and publication, including publications listed below and/or cited throughout the disclosure, as well as U.S. provisional patent application No. 62/147,940, filed Apr. 15, 2015, and PCT/US16/27619, filed Apr. 14, 2016, is expressly incorporated herein by reference in its entirety. Embodiments and variations of this invention other than those specifically disclosed above may be devised by others skilled in the art without departing from the true spirit and scope of the invention. The appended claims include such embodiments and equivalent variations.

What is claimed is:

1. An aqueous metal quenching concentrate composition comprising:
   (a) a water-soluble polyamidopolyamine compound having a molecular weight of about 500 to about 100,000 and at least one to fourteen repeating pendant primary amino groups;
   (b) a ferrous or non-ferrous metal corrosion inhibitor; and
   (c) a hydroxyl-containing diluent.

2. The composition according to claim 1, wherein said polyamidopolyamine is Formula I of FIG. 6A, wherein x, y, and z are additively a number between 3 to about 90, including the endpoints in the range; wherein x', y', z' are additively a number between 3 to about 90, including the endpoints in the range; and wherein a, b, and c are additively a number between 3 to about 90, including the endpoints in the range.

3. The composition according to claim 1, further comprising an additive selected from a coalescing/drying agent, rheology modifier, ester, carboxylic acid, fatty acid, emulsifier, amine, thickener, lubricant, dispersant, antioxidant, alkaline compound, builder, solvent, amphiphatic agent, carrier, biocide, preservative, buffer, metal deactivator, caustic agent, wetting agent, sequestering agent, fungicide, defoamer, antioxidant, die release fluid, antiwear agent, viscosity modifier, de-emulsifier, natural triglyceride, animal fat, vegetable oil, fatty acid ester, phosphate ester, an unreacted polyamine, a non-polymeric polyamine, and combinations thereof.

4. The composition according to claim 1 having a cloud point of about 25 to about 82° C. or 77° F. to about 180° F.

5. The composition according to claim 1, which has a pH of about 8 to about 11.

6. The composition according to claim 1, wherein said corrosion inhibitor is tolyltriazole.

7. The composition according to claim 1, wherein said corrosion inhibitor is sodium nitrite.

8. The composition according to claim 1, wherein said hydroxyl-containing diluent is water.

9. The composition according to claim 3, wherein (a) the polyamidopolyamine is present at between about 5 to about 40% by weight of the total composition and (b) in combination, the corrosion inhibitor and said additive are present at between about 0.1 to 20% by weight of the total composition.

10. The composition according to claim 1, which has at least one property selected from antimicrobial properties, biocidal properties, and bioresistant properties.

11. The composition according to claim 1, which has at least one property selected from defoaming properties or anti-foaming properties.

12. The composition according to claim 10, which has at least one property selected from defoaming properties or anti-foaming properties.

13. The composition according to claim 1, which has at least one property selected from lubricating properties or load carrying properties.

14. The composition according to claim 11, which has at least one property selected from lubricating properties or load carrying properties.

15. The composition according to claim 12, which has at least one property selected from lubricating properties or load carrying properties.

16. An aqueous metal quenching concentrate composition comprising:
   (a) a water-soluble polyamidopolyamine compound of Formula I of FIG. 6A, wherein x, y, and z are additively a number between 3 to about 90, including the endpoints in the range; wherein x', y', z' are additively a number between 3 to about 90, including the endpoints in the range; and wherein a, b, and c are additively a number between 3 to about 90, including the endpoints in the range having a molecular weight of about 500 to about 100,000 and at least one to fourteen repeating pendant primary amino groups; said polyamidopolyamine being present at about 5 to about 40% by weight of said concentrate composition;
   (b) a ferrous or non-ferrous metal corrosion inhibitor, and an optional additive suitable for metal quenching, wherein said inhibitor and said additive, in combination, are present at about 0.1 to 20% by weight of said concentrate composition; and
   (c) the balance, water.

17. The composition according to claim 16, wherein said optional additive is selected from a coalescing/drying agent, rheology modifier, ester, carboxylic acid, fatty acid, emulsifier, amine, thickener, lubricant, dispersant, antioxidant, alkaline compound, builder, solvent, amphiphatic agent, carrier, biocide, preservative, buffer, metal deactivator, caustic agent, wetting agent, sequestering agent, fungicide, defoamer, antioxidant, die release fluid, antiwear agent, viscosity modifier, de-emulsifier, natural triglyceride, animal fat, vegetable oil, fatty acid ester, phosphate ester, an unreacted polyamine, a non-polymeric polyamine, and combinations thereof.

* * * * *